(12) United States Patent
Wu

(10) Patent No.: US 8,317,988 B2
(45) Date of Patent: Nov. 27, 2012

(54) CONCENTRATION DETERMINATION IN A DIFFUSION BARRIER LAYER

(75) Inventor: Huan-Ping Wu, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1238 days.

(21) Appl. No.: 11/734,251

(22) Filed: Apr. 11, 2007

(65) Prior Publication Data

US 2007/0246357 A1 Oct. 25, 2007

Related U.S. Application Data

(63) Continuation of application No. PCT/US2005/036806, filed on Oct. 12, 2005.

(60) Provisional application No. 60/617,889, filed on Oct. 12, 2004, provisional application No. 60/655,180, filed on Feb. 22, 2005.

(51) Int. Cl.
G01N 27/327 (2006.01)

(52) U.S. Cl. ............ 204/403.14; 204/403.02; 204/400

(58) Field of Classification Search ............ 204/403.01–403.15; 205/777.5, 778, 792
See application file for complete search history.

(56) References Cited

U.S. PATENT DOCUMENTS

| | | | |
|---|---|---|---|
| 3,505,136 A | 4/1970 | Attwood | |
| 3,562,041 A | 2/1971 | Robertson | |
| 3,573,139 A | 3/1971 | Eiji Mori et al. | |
| 3,791,988 A | 2/1974 | Bauer et al. | |
| 4,713,165 A | 12/1987 | Conver et al. | |
| 4,746,607 A | 5/1988 | Mura et al. | |
| 4,759,828 A | 7/1988 | Young et al. | |
| 4,897,173 A | 1/1990 | Nankai et al. | |
| 4,929,330 A | 5/1990 | Osaka et al. | |
| 4,929,545 A | 5/1990 | Freitage | |
| 5,112,455 A | 5/1992 | Cozzette et al. | |
| 5,120,420 A | 6/1992 | Nanki et al. | |
| 5,134,057 A * | 7/1992 | Kuypers et al. ............ 430/325 |
| 5,243,516 A | 9/1993 | White | |
| 5,264,103 A | 11/1993 | Yoshioka et al. | |
| 5,312,590 A | 5/1994 | Gunasingham | |
| 5,395,504 A | 3/1995 | Saurer et al. | |
| 5,413,690 A | 5/1995 | Kost et al. | |
| 5,520,786 A | 5/1996 | Bloczynski et al. | |
| 5,560,579 A | 10/1996 | Woodside | |
| 5,582,697 A | 12/1996 | Ikeda et al. | |

(Continued)

FOREIGN PATENT DOCUMENTS

EP 0289269 2/1988

(Continued)

OTHER PUBLICATIONS

Parkes, et al., "Balancing Test Time with accurancy and Percision in blood glucose monitoring How fast is too fast?", Jun. 2003.

(Continued)

*Primary Examiner* — Alex Noguerola
(74) *Attorney, Agent, or Firm* — Blanchard & Associates

(57) ABSTRACT

The present invention relates to improved electrochemical biosensor strips and methods for determining the concentration of an analyte in a sample. By selectively measuring a measurable species residing in a diffusion barrier layer, to the substantial exclusion of the measurable species residing exterior to the diffusion barrier layer, measurement errors introduced by sample constituents, such as red blood cells, and manufacturing variances may be reduced.

22 Claims, 14 Drawing Sheets

U.S. PATENT DOCUMENTS

| | | | |
|---|---|---|---|
| 5,620,579 A | 4/1997 | Genshaw et al. | |
| 5,628,890 A | 5/1997 | Carter et al. | |
| 5,653,863 A | 8/1997 | Genshaw et al. | |
| 5,682,884 A | 11/1997 | Hill et al. | |
| 5,708,247 A | 1/1998 | McAleer et al. | |
| 5,711,861 A | 1/1998 | Ward et al. | |
| 5,773,270 A | 6/1998 | D'Orazio et al. | |
| 5,798,031 A | 8/1998 | Charlton et al. | |
| 5,804,048 A * | 9/1998 | Wong et al. | 204/403.09 |
| 5,820,551 A | 10/1998 | Hill et al. | |
| 5,866,353 A | 2/1999 | Berneth et al. | |
| 5,873,990 A | 2/1999 | Wojciechowski et al. | |
| 5,914,026 A | 6/1999 | Blubaugh, Jr. et al. | |
| 5,951,836 A | 9/1999 | McAleer et al. | |
| 6,143,164 A | 11/2000 | Heller et al. | |
| 6,241,862 B1 * | 6/2001 | McAleer et al. | 204/403.05 |
| 6,284,125 B1 | 9/2001 | Hodges et al. | |
| 6,287,451 B1 | 9/2001 | Winarta et al. | |
| 6,299,757 B1 | 10/2001 | Feldman et al. | |
| 6,325,917 B1 | 12/2001 | Maxwell et al. | |
| 6,338,790 B1 | 1/2002 | Feldman et al. | |
| 6,405,066 B1 | 6/2002 | Essenoreis et al. | |
| 6,461,496 B1 | 10/2002 | Feldman et al. | |
| 6,475,360 B1 | 11/2002 | Hodges et al. | |
| 6,531,040 B2 | 3/2003 | Musho et al. | |
| 6,551,494 B1 | 4/2003 | Heller et al. | |
| 6,576,101 B1 | 6/2003 | Heller et al. | |
| 6,607,658 B1 | 8/2003 | Heller et al. | |
| 6,726,818 B2 | 4/2004 | Cui et al. | |
| 2001/0050228 A1 | 12/2001 | Jaeger et al. | |
| 2002/0092612 A1 | 7/2002 | Davies et al. | |
| 2002/0148739 A2 | 10/2002 | Liamos et al. | |
| 2002/0175075 A1 | 11/2002 | Deng et al. | |
| 2003/0080001 A1 | 5/2003 | Hodges et al. | |
| 2003/0106809 A1 | 6/2003 | Kermani et al. | |
| 2003/0116447 A1 | 6/2003 | Surridge et al. | |
| 2003/0146110 A1 | 8/2003 | Karinka et al. | |
| 2003/0155237 A1 | 8/2003 | Surridge et al. | |
| 2003/0217918 A1 | 11/2003 | Hardwicke et al. | |
| 2004/0003682 A1 | 1/2004 | Nanaumi et al. | |
| 2004/0031698 A1 | 2/2004 | Lee et al. | |
| 2004/0065562 A1 | 4/2004 | Hodges et al. | |

FOREIGN PATENT DOCUMENTS

| | | |
|---|---|---|
| EP | 0396788 A1 * | 11/1990 |
| EP | 0537761 | 4/1993 |
| EP | 0741186 | 11/1996 |
| EP | 0878708 | 11/1998 |
| EP | 1411348 | 4/2004 |
| JP | 55101042 | 8/1980 |
| JP | 6003317 | 1/1994 |
| JP | 6130024 | 5/1994 |
| JP | 2005147990 | 6/2005 |
| WO | WO 8700286 | 1/1987 |
| WO | WO 9109139 | 6/1991 |
| WO | WO 9528634 | 10/1995 |
| WO | WO 9700441 | 1/1997 |
| WO | WO 9719344 | 5/1997 |
| WO | WO 9909404 | 2/1999 |
| WO | 9938003 | 7/1999 |
| WO | WO 9945375 | 9/1999 |
| WO | WO 9946585 | 9/1999 |
| WO | WO 9958709 | 11/1999 |
| WO | WO 0073778 | 7/2000 |
| WO | WO 0060340 | 10/2000 |
| WO | WO 9835225 | 10/2000 |
| WO | 0073785 | 12/2000 |
| WO | WO 0079258 | 12/2000 |
| WO | WO 0133216 | 5/2001 |
| WO | WO 0157510 | 8/2001 |
| WO | WO 0173109 | 10/2001 |
| WO | WO 0173124 | 10/2001 |
| WO | WO 0175438 | 10/2001 |
| WO | WO 03012422 | 2/2002 |
| WO | WO 0232559 | 4/2002 |
| WO | WO 0250609 | 6/2002 |
| WO | WO 03091717 | 4/2003 |
| WO | WO 03044511 | 5/2003 |
| WO | WO 2004027083 | 4/2004 |
| WO | WO 200405125 | 6/2004 |
| WO | WO 2004113902 | 12/2004 |
| WO | WO 2004113917 | 12/2004 |
| WO | WO 2005114164 | 12/2005 |

OTHER PUBLICATIONS

Loeffler, U., et al., "Amperometric biosensors.Characterization of dispersed mediator systems", "Biosens Bioelectronics", 1991, pp. 343-352, vol. 6, No. 4.

Kaku, T., et al.,"Amperometric glucose sensors based on immobilised glucose oxidase polyquinone system" , "Anal. Chem.", 1994, pp. 1231-1235, vol. 66, No. 8, Publisher: American Chemical Society, Published in: USA.

Mukhopadhyay, "The Versatility of Microarrayers", "Anal. Chem.", Sep. 1, 2006, p. 5969, Publisher: American Chemical Society, Published in: USA.

Pedrosa, J.M., et al., "Application of the Cyclic Semi-Integral Voltammetry and Cyclic Semi-Differential Voltammetry to the Determination . . . ", "J. Electroanal. Chem.", 2002, p. 160 vol. 523, Publisher: American Chemical Society, Published in: USA.

Roe J.N., et al., "Bloodless glucose measurements", "Critical Reviews in Therapeutic Drug Carrier Systems", 1998, pp. 199-241, vol. 15, No. 3.

Ng, et al., "Clinical Performance of a New Test with the MediSense Blood Glucose Sensor", 1995, p. S181, vol. 41, No. S6 Part 2.

Collison, Michael E., et al., "Analytical Characterization of Electrochemical Biosensor Test Strips for Measurement of Glucose in lowvol . . . ", "Clinical Chemistry", 1999, pp. 1665-1673, vol. 45, No. 9, Publisher: Washington, D. C.

Dong, S., et al., "Cobalt—porphyrin—Nafion film on carbon microarray electrode to monitor oxygen for enzyme analysis of glucose", "Electroanalysis", 1991, pp. 485-491, vol. 3, No. 6, Publisher: N.Y.

Karalemas, Ioannis D., et al, "Construction and analytical applications of a Si-gold strip enzyme electrode using constant—current potentiometry", "Analytical Letters", 1998, pp. 913-935, vol. 31, No. 6.

Uang, Yuh-Ming, et al, "Criteria for Designing a Polypyrrole Glucose Biosensor by Galvanostatic Electropolymerization", "Electroanalysis", 2001, pp. 1564-1570, vol. 14, No. 22.

Ruan, C., et al, "Detection of zeptomolar concentrations of alkaline phosphatase based on a tyrosinase and horse-radish peroxidase . . . ", "Talanta", 2001, pp. 1095-1103, vol. 54, No. 6.

Cui, Gang, et al., "Differential thick-film amperometric glucose sensor with an enzyme-immobilized nitrocellulose membrane", "Electroanalysis", 2001, pp. 224-228, vol. 13, No. 3.

Zhang C., et al., "Disposable electrochemical capillary-fill device for glucose sensing incorporating a water-soluble enzyme/mediator layer", "Analytica Chimica Acta", 2001, pp. 257-265, vol. 442, No. 2.

Tang Z P, et al., "Effects of drugs on glucose measurements with handheld glucose meters and a portable glucose analyzer", "American Journal of Clinical Pathology", 2000, pp. 75-86, vol. 113, No. 1.

Kawakami, M.; Tanaka, et al, "Effects of nonionic surfactants on electrochemical behavior of ubiquinone and menaquinone incorporated in a carbon paste", "Bioelectrochemistry", , pp. 51-56, vol. 52, No. 1.

Ho, C., et al., "Electrochemical treatment of effluents: a preliminary study of anodic oxidation of simple sugars using lead . . . ", "Journal of Chemical Technology and Biotechnology", 1986, pp. 7-14, vol. 36, No. 1.

Liu, X., et al., "Enzymatic activity of glucose oxidase covalently wired via viologen to electrically conductive polypyrrole films", "Biosens. Bioelectron", 2004, pp. 823-834, vol. 19, No. 8.

Wang J (Reprint), et al., "Enzyme microelctrode arrays strips for glucose and lactate", "Analytical Chemistry", 1994, pp. 1007-1011, vol. 66, No. 7, Publisher: American Chemical Soicety, Published in: USA.

Cui, Gang, et al, "Disposable amperometric glucose sensor electrode with enzyme-immobilized nitrocellulose strip", "Talanta", 2001, pp. 1105-1111, vol. 54, No. 3.

Arens S, et al, "Evaluation of Glucocard Memory 2 and Accutrend Sensor Blood Glucose Meters", "Clinical Chemistry and Laboratory Medicine", 1998, pp. 47-52, vol. 36, No. 1.

Koide, Satoshi, et al, "Electrochemical characterization of an enzyme electrode based on a ferrocene-containing redox polymer", "Journal of Electroanalytical Chemistry", 2001, pp. 193-201, vol. 468, No. 2.

Atanasov P, et al, "Glucose biosensor based on carbon black strips", "Biosensors and bioelectronics", 1991, pp. 361-365, vol. 7, No. 5.

Alexander, P. W., et al., "Enzyme inhibition assays with an amperometric glucose biosensor based on a thiolate self-assembled monolayer", "Electroanalysis", 2000, pp. 343-350, vol. 12, No. 5, Publisher: N.Y.

Kishimoto M, et al, "Clinical usefulness of a non-wiping type glucose meter in diabetic patients", "Diabetes research and clinical practice", 1993, pp. 47-50, vol. 20, No. 1.

Kobayashi, Yuka, et al., "Glucose and lactate biosensors prepared by a layer-by-layer deposition of concanavalin a and mannose-labeled enzymes . . . ", "Chemical and Pharmaceutical Bulletin", 2001, pp. 755-757, vol. 49, No. 6.

Bruns W., "Implications of an intracorporeal glucose sensor in the management of diabetic patients", "Biomedica Acta", 1989, pp. 925-933, vol. 48, No. 11-12.

Gerritsen, M.; Jansen, et al., "Influence of inflammatory cells and serum on the performance of implantable glucose sensors", "Journal of Biomedical Materials Research", 2000, pp. 69-75, vol. 54, No. 1.

Kost G J, et al, "Multicenter study of oxygen-insensitive handheld glucose point-of-care testing in critical care/ hospital/ambulatory . . . ", "Critical care medicine", 1998, pp. 581-590, vol. 26, No. 3.

Iwuoha, E. I., et al., "Novel electron transfer mediators for amperometric bioelectrodes: introduction of methylsquarate and phenylsquarate", "Electroanalysis", 2002, pp. 1177-1184, vol. 14, No. 17, Publisher: N.Y.

Urban, G.; Jobst, et al, "Performance of integrated glucose and lactate thin-film microbiosensors for clinical analyzers", "Sensors and Actuators, B: Chemical", 1994, pp. 592-596, vol. 19, No. 1-3.

Owens, George S., et al., "Pulsed electrochemical detection of sulfur-containing compounds following microbore liquid chromatography", "Current Separations", 1996, pp. 82-88, vol. 14, No. 3/4.

Dalrymple-Alford, P., et al., "Peak Shapes in Semi-differential Electroanalysis", "Anal. Chem.", 1977, pp. 1390-1394, vol. 49, No. 9, Publisher: American Chemical Society, Published in: USA.

Goto, M., et al., "Semi-integral Electroanalysis: Shapes of Neopolarograms", "Anal. Chem.", 1973, p. 2043 vol. 45, No. 12, Publisher: American Chemical Society, Published in: USA.

Wang, Joseph [Reprint Author], et al, "Single-use thick-film electrochemical sensor for insulin", "Electroanalysis", 2002, pp. 1365-1368, vol. 14, No. 19-20.

EPO, "Search Report and Written Opinion for PCT/US2005/036806", 02/20/06, Publisher: International Searching Authority.

Australian Government—IP Australia, "Examiner's First Report on Patent Application No. 2005295106", Aug. 30, 2010, Published in: Australia.

Government of India Patent Office, "Hearing Notice in Reference of Application No. 476/MUMNP/2007", Aug. 10, 2010, Published in: India.

Cui, et al, "Disposable amperometric glucose sensor electrode with enzyme-immobilized nitrocellulose strip", "Talanta", 2001, pp. 1105-1111, vol. 54, No. 3.

Hall, Elizabeth A. H., "Abstract of 'The Microcomputer-Controlled Electrochemical Sensor'", "J. Microcomputer Applications", 1984, pp. 319-237, vol. 7, No. 3-4.

IUPAC Compendium of Chemical Technology, "Hydrophobic Interaction", 1994.

Kunzler, Jay Friedrich, "Hydrogels", "Encyclopedia of Polymer Science and Technology", Mar. 15, 2002, pp. 691-722, vol. 2, Publisher: John Wiley & Sons, Inc., Published in: United States.

Intellectual Property Office of New Zealand, "Examination Report", Jun. 8, 2009, Published in: New Zealand.

\* cited by examiner

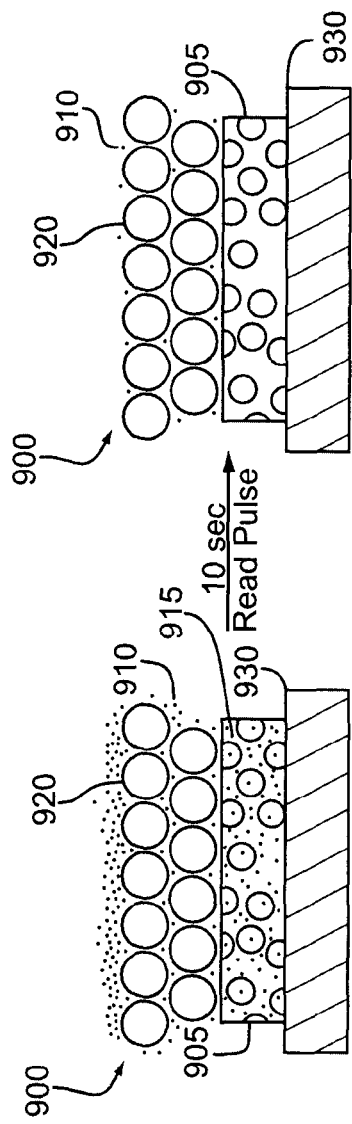
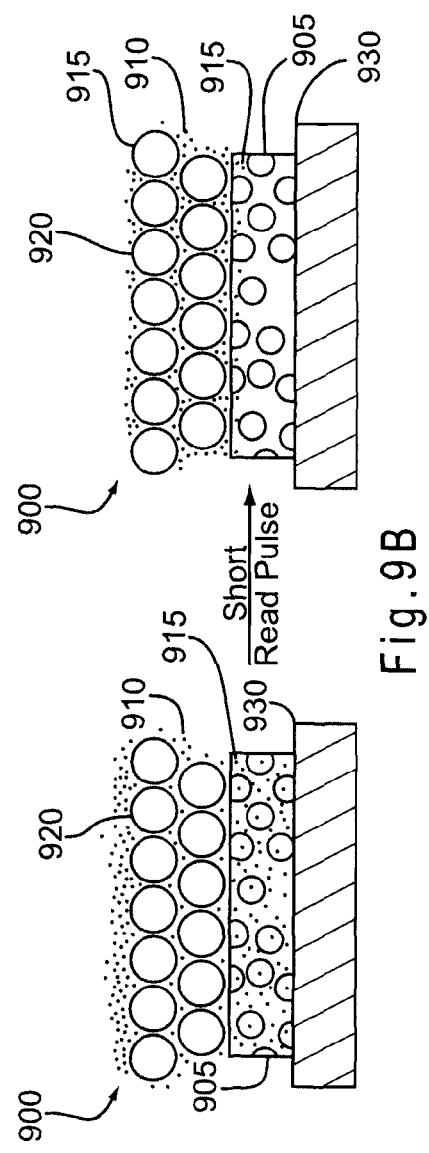
Fig.9A
Fig.9B

|    | 10 second Read Pulse |       |       |       |          | 1 second Read Pulse |        |       |       |          | Bias Reduction (%) |
|----|------|------|------|------|----------|--------|-------|-------|-------|----------|-----------|
|    | 50   | 100  | 200  | 400  | Avg Bias | 50     | 100   | 200   | 400   | Avg Bias |           |
| 1  | 18.6 | 37.5 |      | 53.46| 36.53    | -2.4   | 15    |       | 23.06 | 11.9     | 67.44     |
| 2  | 2.6  | 6.8  |      | 42.85| 17.4     | -15.3  | -4.9  |       | 41.6  | 7.1      | 58.96     |
| 3  | 26.2 | 35.3 |      | 34.6 | 32       | 9.3    | 11.2  |       | 28.8  | 16.4     | 48.63     |
| 4  | 19.8 | 33   |      | 32.2 | 28.4     | -0.1   | 16    |       | 15.8  | 10.6     | 62.74     |
| 5  | 6.93 | 30.92|      | 38.43| 25.42    | -15.27 | 17.2  |       | 5.27  | 2.4      | 90.57     |
| 6  | 26.02| 51.79|      | 72.36| 50.05    | 3.45   | 26.54 |       | 44.06 | 24.68    | 50.69     |
| 7  | 28.84| 46.97|      | 73.86| 49.89    | 10.69  | 30.08 |       | 55.69 | 32.15    | 35.56     |
| 8  | 6.42 | 35.02| 54.5 | 57.55| 38.37    | -15.19 | 16.03 | 35.16 | 10.23 | 11.56    | 69.88     |
| 9  | 30.83| 45.52| 44.49| 44.02| 41.22    | 24.58  | 44.38 | 35.2  | 22.4  | 31.64    | 23.24     |
| 10 | 27.69| 26.57| 34.69| 39.19| 32.04    | 0.62   | -12.9 | 22.03 | 28.54 | 9.57     | 70.12     |
| 11 | 47.81| 50.62| 61.12| 59.21| 54.69    | 11.94  | 15.76 | 31    | 40.58 | 24.82    | 54.62     |
| 12 | 43.04| 71.63| 71.02| 65.64| 62.83    | 18.2   | 33.74 | 36.35 | 44.89 | 33.29    | 47.01     |
| 13 | 16.08| 13.19| 47.69| 52.52| 32.37    | -12.6  | 9.33  | 25.79 | 40.02 | 15.64    | 51.69     |
| 14 | 7.12 | 32.24| 44.75| 51.21| 33.83    | -11.46 | 9.08  | 30.96 | 40.68 | 17.32    | 48.82     |
| 15 | -0.48| 9.2  | 42.8 | 45.63| 24.29    | -11.84 | 2.46  | 38.14 | 38.79 | 16.89    | 30.47     |
| 16 | 16.65| 32.87| 40.72| 30.68| 30.23    | 0.88   | 12.18 | 21.8  | 33.71 | 17.14    | 43.3      |
| 17 | -1.18| 38.75| 51.86| 70.02| 39.86    | -27.27 | 12.67 | 24.16 | 47.27 | 14.21    | 64.36     |
| 18 | 56.88| 93.75| 78.6 | 77.14| 76.59    | 23.36  | 45.99 | 42.02 | 46.07 | 39.36    | 48.61     |
| 19 | 23.79| 35.17| 47.23| 57.69| 40.97    | -5.07  | 5.6   | 30.47 | 34.25 | 16.31    | 60.18     |
| 20 | 20.72| 33.07| 53.1 | 55.28| 40.54    | -14.11 | 5.56  | 31.84 | 39.14 | 15.61    | 61.5      |
| 21 | 18.19| 21.19| 33.42| 39.41| 28.05    | -6.16  | -1.94 | 18.72 | 36.75 | 11.84    | 57.78     |
| 22 | 22.31| 22.09| 37.74| 39.99| 30.53    | -8.59  | -7.56 | 33.71 | 54.01 | 17.89    | 41.39     |
| 23 | 56.53| 51.14| 33.52| 30.27| 42.87    | 26.7   | 15.94 | 37.49 | 56.05 | 34.05    | 20.58     |
| 24 | 38.63| 57   | 56.52| 56.57| 52.18    | 13.35  | 13.92 | 30    | 37.49 | 23.69    | 54.6      |
| 25 | -7.53| 17.23| 39.26| 53.24| 25.55    | -29.85 | 3.52  | 29.79 | 46.04 | 12.38    | 51.57     |
| 26 | 38.26| 53.5 | 57.71| 56.42| 51.47    | 7.58   | 18.87 | 28.72 | 34.02 | 22.3     | 56.68     |
| 27 | -2.43| 27.72| 50.71| 53.16| 32.29    | -15.9  | 3.56  | 35.95 | 42.93 | 16.63    | 48.48     |
| 28 | 40.41| 55.55| 46.16| 51.23| 48.34    | 6.35   | 15.17 | 25.73 | 41.91 | 22.29    | 53.89     |
| 29 | 17.1 | 32.74| 58.15| 67.64| 43.91    | -23.8  | -0.67 | 44.21 | 55.16 | 18.72    | 57.35     |
| 30 | 8.92 | 30.32| 32.7 | 48.09| 30.01    | -6.61  | 16.28 | 35.8  | 48.81 | 23.57    | 21.46     |
| 31 | 5.75 | 31.54| 44.94| 57.71| 34.98    | -29.54 | 30.31 | 42.45 | 56.01 | 24.81    | 29.09     |
| 32 | 0.25 | 5.7  | 11.11| 26.79| 10.96    | -4.4   | -1.72 | 1.69  | 27.09 | 5.66     | 48.33     |
| 33 | 1.19 | 2.87 | 5.66 | 10.87| 5.15     | -5.32  | -0.28 | -2.92 | 14.71 | 1.55     | 69.99     |
| 34 | 10.01| 34.95| 60.03| 54.07| 39.76    | -2.53  | 17.58 | 46.25 | 41.26 | 25.64    | 35.51     |
| 35 | 27.66| 38.11| 80.72| 84.21| 57.67    | 12.68  | 15.69 | 57.99 | 61.93 | 37.08    | 35.72     |
| 36 | 7.88 | 7.51 | 43.07| 38.97| 24.36    | 0.1    | -3.91 | 34.85 | 29.6  | 15.16    | 37.76     |
| Ave|      |      |      |      |          |        |       |       |       |          | 50.24     |

Fig.12

Precision Comparison

| A | Slope | | | | | Intercept | | | |
|---|---|---|---|---|---|---|---|---|---|
| 2-4-x | 1 sec | 5 sec | 10 sec | 15 sec | | 1 sec | 5 sec | 10 sec | 15 sec |
| 1 mil | 17.625 | 11.696 | 9.521 | 8.042 | 1 mil | 2426 | 1282.3 | 963.34 | 814.11 |
| 3 mil | 17.835 | 11.965 | 10.013 | 8.8584 | 3 mil | 2374.5 | 1226 | 894.65 | 751.68 |
| 5 mil | 17.408 | 12.07 | 10.334 | 9.267 | 5 mil | 2268 | 1147.5 | 779 | 613.64 |
| 10 nil | 17.789 | 12.282 | 10.406 | 9.3369 | 10 nil | 2527 | 1243.5 | 835.45 | 646.3 |
| Ave | 17.66 | 12.00 | 10.07 | 8.88 | | 2398.88 | 1224.83 | 868.11 | 706.43 |
| StDev | 0.19 | 0.24 | 0.40 | 0.59 | | 107.82 | 56.66 | 79.12 | 92.86 |
| %-CV | 1.09 | 2.03 | 4.00 | 6.70 | | 4.49 | 4.63 | 9.11 | 13.14 |

| B | Slope | | | | | Intercept | | | |
|---|---|---|---|---|---|---|---|---|---|
| 4-2-x | 1 sec | 5 sec | 10 sec | 15 sec | | 1 sec | 5 sec | 10 sec | 15 sec |
| 1 mil | 14.316 | 10.541 | 8.6459 | 7.4083 | 1 mil | 1600 | 922.18 | 704.06 | 617.93 |
| 3 mil | 14.487 | 10.887 | 9.4164 | 8.2635 | 3 mil | 1490.4 | 815.49 | 511.94 | 458.69 |
| 5 mil | 14.457 | 10.949 | 9.7811 | 8.9251 | 5 mil | 1551.3 | 813.45 | 401.4 | 279.92 |
| 10 nil | 13.882 | 10.785 | 9.6788 | 8.8721 | 10 nil | 1650.1 | 828.27 | 413.41 | 274.49 |
| Ave | 14.29 | 10.79 | 9.38 | 8.37 | | 1572.95 | 844.85 | 507.70 | 407.76 |
| StDev | 0.28 | 0.18 | 0.51 | 0.71 | | 68.23 | 51.97 | 139.96 | 164.18 |
| %-CV | 1.95 | 1.66 | 5.47 | 8.44 | | 4.34 | 6.15 | 27.57 | 40.27 |

Fig. 15

CONCENTRATION DETERMINATION IN A DIFFUSION BARRIER LAYER

REFERENCE TO RELATED APPLICATIONS

This application is a continuation of PCT/US2005/036806 entitled "Concentration Determination in A Diffusion Barrier Layer" filed Oct. 12, 2005, which was published in English and claimed the benefit of U.S. Provisional Application No. 60/617,889 entitled "Concentration Determination in A Diffusion Barrier Layer" filed Oct. 12, 2004 and U.S. Provisional Application No. 60/655,180 entitled "Concentration Determination in A Diffusion Barrier Layer" filed Feb. 22, 2005.

BACKGROUND

In monitoring medical conditions and the response of patients to treatment efforts, it is desirable to use analytical methods that are fast, accurate, and convenient for the patient. Electrochemical methods have been useful for quantifying certain analytes in body fluids, particularly in blood samples. Typically, these biological analytes, such as glucose, undergo redox reactions when in contact with specific enzymes. The electric current generated by such redox reactions may be correlated with the concentration of the biological analyte in the sample.

Tiny electrochemical cells have been developed that provide patients the freedom to monitor blood analyte concentrations without the need of a healthcare provider or clinical technician. Typical patient-operated electrochemical systems utilize a disposable sensor strip with a dedicated measurement device containing the necessary circuitry and output systems. For analysis, the measurement device is connected to the disposable electrochemical sensor strip containing the electrodes and reagents to measure the analyte concentration in a sample that is applied to the strip.

The most common of these miniature electrochemical systems are glucose sensors that provide measurements of blood glucose levels. Ideally, a miniature sensor for glucose should provide accurate readings of blood glucose levels by analyzing a single drop of whole blood, typically from 1-15 microliters (μL).

In a typical analytical electrochemical cell, the oxidation or reduction half-cell reaction involving the analyte produces or consumes electrons, respectively. This electron flow can be measured, provided the electrons can interact with a working electrode that is in contact with the sample to be analyzed. The electrical circuit is completed through a counter electrode that is also in contact with the sample. A chemical reaction also occurs at the counter electrode, and this reaction is of the opposite type (oxidation or reduction) relative to the type of reaction at the working electrode. Thus, if oxidation occurs at the working electrode, reduction occurs at the counter electrode. See, for example, *Fundamentals Of Analytical Chemistry*, 4$^{th}$ Edition, D. A. Skoog and D. M. West; Philadelphia: Saunders College Publishing (1982), pp 304-341.

Some conventional miniaturized electrochemical systems include a true reference electrode. In these systems, the true reference electrode may be a third electrode that provides a non-variant reference potential to the system, in addition to the working and counter electrodes. While multiple reference electrode materials are known, a mixture of silver (Ag) and silver chloride (AgCl) is typical. The materials that provide the non-variant reference potential, such as a mixture of silver and silver chloride, are separated, by their insolubility or other means, from the reaction components of the analysis solution.

In other miniature electrochemical systems, a combination counter/reference electrode is employed. These electrochemical sensor strips are typically two electrode systems having a working electrode and a counter/reference electrode. The combined counter/reference electrode is possible when a true reference electrode also is used as the counter electrode.

Because they are true reference electrodes, counter/reference electrodes are typically mixtures of silver (Ag) and silver chloride (AgCl), which exhibit stable electrochemical properties due to the insolubility of the mixture in the aqueous environment of the analysis solution. Since the ratio of Ag to AgCl does not significantly change during transient use, the potential of the electrode is not significantly changed.

An electrochemical sensor strip is typically made by coating a reagent layer onto the conductor surface of an analysis strip. To facilitate manufacturing, the reagent layer may be coated as a single layer onto all of the electrodes.

The reagent layer may include an enzyme for facilitating the oxidation or reduction reaction of the analyte, as well as any mediators or other substances that assist in the transfer of electrons between the analyte reaction and the conductor surface. The reagent layer also may include a binder that holds the enzyme and mediator together, thus allowing them to be coated onto the electrodes.

Whole blood (WB) samples contain red blood cells (RBC) and plasma. The plasma is mostly water, but contains some proteins and glucose. Hematocrit is the volume of the RBC constituent in relation to the total volume of the WB sample and is often expressed as a percentage. Whole blood samples generally have hematocrit percentages ranging from 20 to 60%, with ~40% being the average.

One of the drawbacks of conventional electrochemical sensor strips utilized to measure the glucose concentration in WB is referred to as the "hematocrit effect." The hematocrit effect is caused by RBC blocking the diffusion of the mediator or other measurable species to the conductor surface for measurement. Because the measurement is taken for the same time period each time a sample is tested, blood samples having varying concentrations of RBC can cause inaccuracies in the measurement. This is true because the sensor cannot distinguish between a lower measurable species concentration and a higher measurable species concentration where the RBC interfere with diffusion of the measurable species to the conductor surface. Thus, variances in the concentration of RBC in the WB sample result in inaccuracies (the hematocrit effect) in the glucose reading.

If WB samples containing identical glucose levels, but having hematocrits of 20, 40, and 60%, are tested, three different glucose readings will be reported by a conventional system that is based on one set of calibration constants (slope and intercept, for instance). Even though the glucose concentrations are the same, the system will report that the 20% hematocrit sample contains more glucose than the 60% hematocrit sample due to the RBC interfering with diffusion of the measurable species to the conductor surface.

Conventional systems are generally configured to report glucose concentrations assuming a 40% hematocrit content for the WB sample, regardless of the actual hematocrit content in the blood sample. For these systems, any glucose measurement performed on a blood sample containing less or more than 40% hematocrit will include some inaccuracy attributable to the hematocrit effect.

Conventional methods of reducing the hematocrit effect for amperometric sensors include the use of filters, as disclosed in US. Pat. Nos. 5,708,247 and 5,951,836; reversing the potential of the read pulse, as disclosed in WO 01/57510; and by methods that maximize the inherent resistance of the sample, as disclosed in U.S. Pat. No. 5,628,890. While each of these methods balance various advantages and disadvantages, none are ideal.

As can be seen from the above description, there is an ongoing need for improved devices and methods for determining the concentration of biological analytes, including glucose. The devices and methods of the present invention may decrease the error introduced by the hematocrit and other effects in WB samples.

SUMMARY

In one aspect, an electrochemical sensor strip is provided that includes a base and first and second electrodes on the base. The first electrode includes at least one first layer on a first conductor, where the first layer includes an oxidoreductase enzyme and a binder. The thickness of the first layer is selected so that when a read pulse is applied to the first and second electrodes during use, measurable species are substantially detected within the first layer and are not substantially detected external to the first layer.

In another aspect, a method of increasing the accuracy of quantitative analyte determination is provided. The method includes providing an electrochemical sensor strip having at least one first layer including an oxidoreductase enzyme, a mediator, and a binder. An analyte containing sample is then introduced to the electrochemical sensor strip and an electric potential is applied in the form of a read pulse. The duration of the read pulse substantially detects the ionized form of the mediator within the first layer while substantially excluding from detection the ionized form of the mediator external to the first layer.

In one embodiment, an electrochemical sensor strip is provided, comprising: a base; a first electrode on the base, where the first electrode comprises at least one first layer on a first conductor, the first layer including a reagent layer; and a second electrode on the base, the thickness of the first layer selected so that a read pulse applied to the first and second electrodes during use substantially detects a measurable species within the first layer and substantially does not detect the measurable species external to the first layer.

In another embodiment, the electrochemical sensor strip further comprises a second layer between the first conductor and the first layer, the thickness of the second layer selected so that a read pulse applied to the first and second electrodes during use substantially detects the measurable species within the second layer and substantially does not detect the measurable species external to the second layer, including the measurable species within the first layer, where the thickness of the first layer is not selected so that a read pulse applied to the first and second electrodes during use substantially detects the measurable species within the first layer. The second layer may be at least 5 μm or from 8 to 25 μm thick. In another aspect, the second layer may be at least 1 μm or from 5 to 25 μm thick. The second layer may not include the oxidoreductase enzyme and/or a mediator, but may include a polymeric material.

In another embodiment, a method of increasing the accuracy of quantitative analyte determination is provided comprising: providing an electrochemical sensor strip having a base, a first conductor on the base, a second conductor on the base, and at least one first layer on at least the first conductor, where the at least one first layer includes a reagent layer including a binder; introducing an analyte containing sample having a liquid component to the electrochemical sensor strip, where the sample provides electrical communication between the first and second conductors; applying an electric potential between the first and second conductors in the form of a read pulse, the read pulse applied for a duration that substantially detects a measurable species within the first layer and substantially does not detect the measurable species external to the first layer; measuring the read pulse to provide a quantitative value of the analyte concentration in the sample with increased accuracy in relation to an electrochemical sensor strip that substantially detects the measurable species external to the first layer. An initial pulse and a time delay may be applied before the read pulse.

In another embodiment, an electrochemical sensor strip is provided, comprising: a base; a first electrode on the base, where the first electrode comprises at least one first layer on a first conductor, the first layer including a mediator, a binder, and at least one of glucose oxidase, glucose dehydrogenase, and mixtures thereof; and a second electrode on the base comprising a soluble redox species, the soluble redox species including at least one of an organotransition metal complex, a transition metal coordination metal complex, and mixtures thereof, the thickness of the first layer selected so that a read pulse applied to the first and second electrodes during use substantially detects a measurable species within the first layer and substantially does not detect the measurable species external to the first layer. The second electrode of the electrochemical sensor strip may comprise a second redox species on a second conductor, where the soluble redox species is a first redox species of a redox pair including the first species and the second species, and where the molar ratio of the first redox species to the second redox species is greater than about 1.2:1.

In another embodiment, an electrochemical sensor strip is provided, comprising: a base; a lid contacting the base to define a gap; a first electrode on the base including a first conductor; a second layer on the first conductor, where a reagent layer does not reside between the first conductor and the second layer; a second electrode on the base; and a reagent layer in the gap, the thickness of the second layer selected so that a read pulse applied to the first and second electrodes during use substantially detects a measurable species within the second layer and substantially does not detect the measurable species external to the first layer.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like references numerals generally designate corresponding parts throughout the different views.

FIGS. 9A and 9B depict a working electrode having a conductor surface and a DBL during the application of long and short read pulses.

FIG. 12 is a table comparing the bias results for 1 and 10 second read pulses from multiple analyses performed with multiple types of sensor strips having a diffusion barrier layer.

FIG. 15 compares the precision between sensor strips having a DBL and gap volumes of 1, 3, 5, and 10 mL when read pulses of 1, 5, 10, and 15 seconds were applied.

DETAILED DESCRIPTION

Tiny electrochemical cells provide patients with the benefit of nearly instantaneous measurement of their glucose levels. One of the main reasons for errors in these measurements is the hematocrit effect. The hematocrit effect arises when red blood cells randomly affect the diffusion rate of measurable species to the conductor surface of the working electrode.

By measuring a measurable species residing in a diffusion barrier layer (DBL), to the substantial exclusion of the measurable species residing exterior to the DBL, measurement errors introduced by the hematocrit effect and manufacturing variances may be reduced. Substantial exclusion of the measurable species external to the DBL may be achieved by selecting the thickness of the DBL on the basis of the read pulse duration or by selecting the duration of the read pulse on the basis of the thickness of the DBL.

Figure 1:
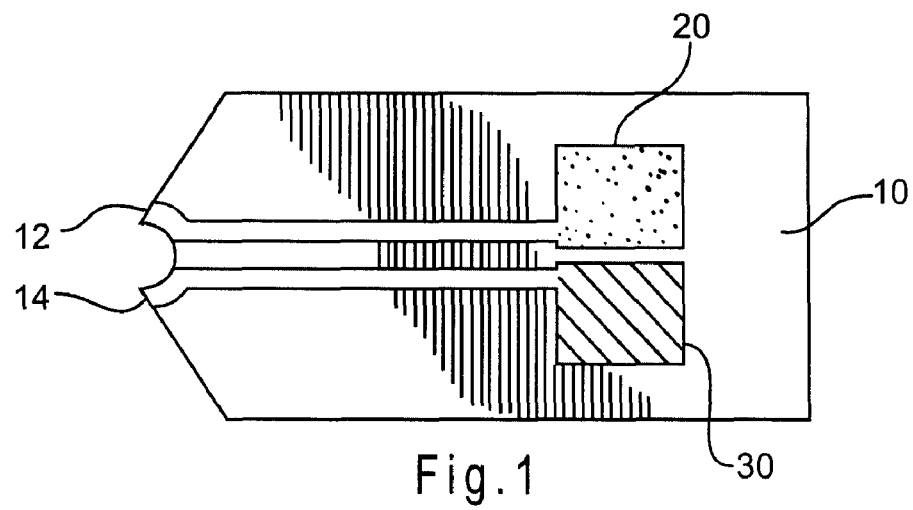
FIG. 1 is a top view diagram of a sensor base containing a working electrode and a counter electrode.
Figure 2:
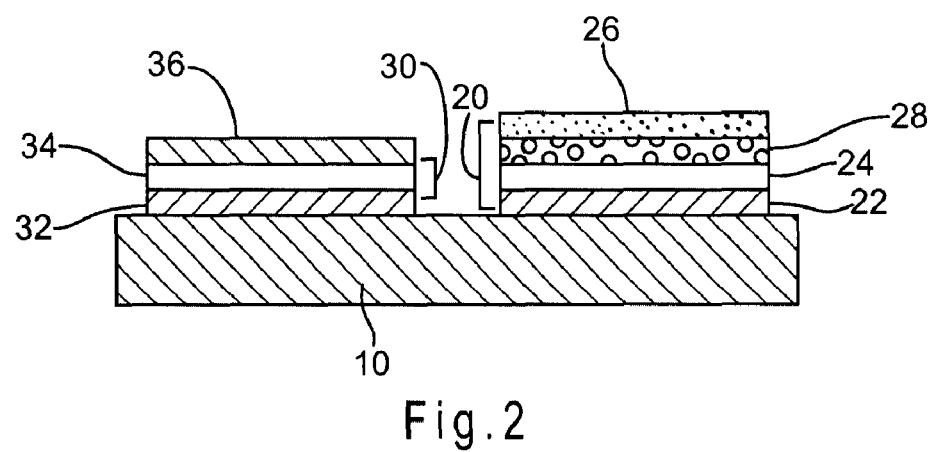
FIG. 2 is an end view diagram of the sensor base of FIG. 1.

FIG. 1 is a top view diagram of a sensor base 10 having conductors 12 and 14 that contains a working electrode 20 and a counter electrode 30. FIG. 2 is an end view diagram of the sensor base 10, depicting the working electrode 20 and the counter electrode 30. The working electrode 20 may include a first main conductor 22, while the counter electrode 30 may include a second main conductor 32. Optionally, surface conductors 24 and 34 may reside on the main conductors 22 and 32, respectively. A diffusion barrier layer (DBL) 28 also may reside on the main conductor 22 of the working electrode 20.

In one aspect, the main conductors 22 and 32 may include metal foil that is contiguous with the surface conductors 24 and 34 that include one or more layers of conductive carbon powder. The working electrode 20 may include a first reagent layer 26 residing on the first main conductor 22, while the counter electrode 30 may include a second reagent layer 36 residing on the second main conductor 32. In another aspect, the counter electrode 30 may be a counter/reference electrode or a counter electrode coated with a soluble redox species having a known oxidation or reduction potential. The sensor base 10 may have other configurations, including those with fewer or additional components as is known in the art. For additional sensor designs, see, for example, U.S. Pat. Nos. 5,120,420 and 5,798,031, both of which are incorporated by reference.

The sensor base 10 is preferably an electrical insulator that may isolate the electrochemical system from its surroundings. In use, the working electrode 20 and the counter electrode 30 are in electrical communication with a measurement device (not shown) through the conductors 12 and 14, respectively. The measurement device may apply an electrical potential between the working electrode 20 and the counter electrode 30. The measurement device then may quantify the electrical current flowing between the working electrode 20, a sample (not shown), and the counter electrode 30. The sample may establish electrical communication between the electrodes 20, 30.

The main conductors 22 and 32 and the optional surface conductors 24 and 34 of electrodes 20 and 30 may contain any electrically conductive substance, including metals, conductive polymers, and conductive carbon. Examples of electrically conductive substances include a thin layer of a metal, such as gold, silver, platinum, palladium, copper, or tungsten, as well as a thin layer of conductive carbon powder. Preferably, conductors that are in contact with the sample during the use of the sensor are made of inert materials, such that the conductor does not undergo a net oxidation or a net reduction during the analysis. More preferably, electrodes that are in contact with the sample during the use of the sensor are made of non-ionizing materials, such as carbon, gold, platinum, and palladium.

Metals may be deposited on the base 10 by deposition of a metal foil, by chemical vapor deposition, or by deposition of a slurry of the metal. Conductive carbon may be deposited on the base 10, for example, by pyrolysis of a carbon-containing material or by deposition of a slurry of carbon powder. The slurry may contain more than one type of electrically conductive substance. For example, the slurry may contain both palladium and carbon powder. In the case of slurry deposition, the fluid mixture may be applied as an ink to the base material, as described in U.S. Pat. No. 5,798,031.

When the surface conductors 24 and 34 are deposited on the main conductors 22 and 32, it is preferred that the substance from which the surface conductors are made is a non-ionizing conductive material. When the main conductors 22 and 32 are utilized without the distinct surface conductors 24 and 34, it is preferred that the conductive material from which the main conductors are made is non-ionizing. More preferably, the portion of the counter electrode 30 in contact with the second reagent layer 36 (either the main conductor 32 or the surface conductor 34) is a non-ionizing material.

A DBL may be integral to the reagent layer 26 or it may be a distinct layer 28 as depicted in FIG. 2. Thus, the DBL may be formed as a combination reagent/diffusion barrier layer on the conductor surface, as a distinct layer on the conductor surface, as a distinct layer on the conductor surface on which the reagent layer resides, or as a distinct layer on the reagent layer.

The DBL provides a porous space having an internal volume where a measurable species may reside. The pores of the DBL are selected so that the measurable species may diffuse into the DBL, while physically larger sample constituents, such as RBC, are substantially excluded. Although conventional sensor strips have used various materials to filter RBC from the working electrode, the DBL of the present invention additionally provides an internal porous space to contain and isolate a portion of the measurable species from the sample volume.

By controlling the length of the measurement reaction at the conductor surface, the sensor strip may measure the measurable species internal to the DBL, while substantially excluding from measurement the measurable species external to the DBL. In relation to the conductor surface, the internal volume of the DBL alters the physical parameter of the diffusion rate of the measurable species it contains in relation to the diffusion rate of the measurable species outside of the DBL.

Because the measurable species internal to the DBL diffuses at a different rate to the conductor surface than the measurable species external to the DBL, the length of the measurement reaction at the working electrode selects which measurable species is preferentially measured. While identical from a molecular standpoint, the different diffusion rates of the measurable species internal and external to the DBL allow their substantial differentiation.

Because the reagent layer 26 of the working electrode 20 may include a binder, any portion of the binder that does not solubilize into the sample prior to the application of a read pulse can function as the DBL. When the reagents are combined with the binder material to provide both support to the reagents and to provide the DBL, the binder material is preferably a polymeric material that is at least partially water soluble. In this manner, a portion of the binder material can solubilize, while the remainder of the binder material may remain on the main conductor 22 to function as the DBL.

Suitable partially water soluble polymeric materials include, but are not limited to, poly(ethylene oxide) (PEO), carboxy methyl cellulose (CMC), polyvinyl alcohol (PVA), hydroxyethyl cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids such as polylysine, polystyrene sulfonate, gelatin, acrylic acid, methacrylic acid, starch, and maleic anhydride salts thereof, derivatives thereof, and combinations thereof. Among the above, PEO, PVA, CMC, and HEC are preferred at present, with CMC and PEO being especially preferred at present.

Materials that were conventionally used to form filters for the exclusion of RBC from the working electrode also may be used in the DBL. This may be achieved by increasing the thickness of the material or by reducing the length of the measurement reaction at the working electrode in relation to when the material was used as filter. It also may be accomplished by forming the material in a manner that modifies its viscosity, such as through the introduction of salts like sodium or potassium chloride.

In another aspect, the DBL may be the distinct DBL 28. The distinct layer 28 may have an average initial thickness of at least 5 µm, preferably, from 8 to 25 µm, and more preferably from 8 to 15 µm. In another aspect, the distinct layer 28 may have an average initial thickness of at least 1 µm or preferably from 5 to 25 µm. When the DBL is a distinct layer, it may be made from a partially soluble polymeric material, such as the same material utilized as a binder in the reagent layer 26, but lacking the reagents. The distinct layer 28 may be any material that provides the desired pore space, but that is partially or slowly soluble in water during use of the sensor.

Although not shown in the figures, when the DBL is the distinct layer 28 the reagent layer 26 may not reside on the distinct layer 28. Instead, the reagent layer 26 may reside on any portion of the sensor strip that allows the reagent to solubilize in the sample. For example, the reagent layer 26 may reside on the sensor base 10 or on a lid 50, as discussed below with regard to FIG. 8.

In one aspect, the first and second reagent layers may include the same constituents and may reside on both the first and second main conductors 22, 32. When the reagent layers 26 and 36 for the working and counter electrodes, 20 and 30 respectively, have different compositions, the reagent layer for each electrode may be separately optimized. Thus, the first reagent layer 26 may contain ingredients that facilitate the reaction of the analyte and the communication of the results of this reaction to the first main conductor 22.

Similarly, the second reagent layer 36 may contain ingredients that facilitate the free flow of electrons between the sample being analyzed and the second main conductor 32. For example, a soluble redox species incorporated into the second reagent layer 36 may undergo an opposite redox reaction to the analyte. Even though the redox species is being consumed (i.e. converted into its counterpart species) during use, it may be present in a high enough concentration in the second reagent layer 36 to provide a relatively constant linear relationship between the measured current and the analyte concentration for the time scale of the analysis. Thus, improved performance may be obtained by separately optimizing the reagent layers 26 and 36 in comparison to sensor strips utilizing the same reagent layer for both electrodes.

A large molar ratio of the soluble redox species placed on the counter electrode 30 may increase the shelf life of the sensor strip. A small degree of spontaneous conversion of the soluble redox species into its counterpart species can occur during the time between the manufacture of the strip and its use with a sample. Since the relative concentration will remain high due to the excess soluble redox species, the sensor may produce accurate results after storage.

The first reagent layer 26 residing on the first main conductor 22 may include an oxidoreductase. The oxidoreductase may be specific for the analyte of interest. The oxidoreductase may be specific for a substrate such that the reaction of the oxidoreductase and its substrate is affected by the presence or amount of the analyte of interest. While in a formal sense a substrate is affected by the amount of the analyte, unless stated otherwise, the term analyte is intended to include an actual analyte present in the sample or its substrate in this description and the appended claims.

Examples of oxidoreductases and their specific analytes are given below in Table I.

TABLE I

| Oxidoreductase (reagent layer) | Substrate/analyte |
| --- | --- |
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

For example, an alcohol oxidase can be used in a reagent layer to provide a sensor that is sensitive to the presence of alcohol in a sample. Such a system could be useful in measuring blood alcohol concentrations. In another example, glucose dehydrogenase or glucose oxidase can be used in the reagent layer to provide a sensor that is sensitive to the presence of glucose in a sample. This system could be useful in measuring blood glucose concentrations, for example in patients known or suspected to have diabetes. If the concentrations of two different substances are linked through a known relationship, then the measurement of one of the substances through its interaction with the oxidoreductase can provide for the calculation of the concentration of the other substance. For example, an oxidoreductase may provide a sensor that is sensitive to a particular substrate, and the measured concentration of this substrate can then be used to calculate the concentration of the analyte of interest.

The first reagent layer 26 may include a mediator. Without wishing to be bound by any theory of interpretation, it is believed that mediators may act either as a redox cofactor in the initial enzymatic reaction or as a redox collector to accept electrons from or donate electrons to the enzyme or other species after the reaction with the analyte has occurred. In the situation of a redox cofactor, the mediator is believed to be the species that balances the redox reaction of the analyte. Thus if the analyte is reduced, the mediator is oxidized. In the situation of a redox collector, another species may have been oxidized or reduced initially to balance the redox reaction of the analyte. This species may be the oxidoreductase itself, or it may be another species such as a redox cofactor.

Mediators in enzymatic electrochemical cells are described in U.S. Pat. No. 5,653,863, for example, which is incorporated herein by reference. In some cases, the mediator may function to regenerate the oxidoreductase. In one aspect, if the enzyme oxidizes an analyte, the enzyme itself is reduced. Interaction of this enzyme with a mediator can result in reduction of the mediator, together with oxidation of the enzyme to its original, unreacted state. Interaction of the mediator with the working electrode 20 at an appropriate electrical potential can result in a release of one or more electrons to the electrode together with oxidation of the mediator to its original, unreacted state.

Examples of mediators include OTM and coordination complexes, including ferrocene compounds, such as 1,1'-dimethyl ferrocene; and including complexes described in U.S. Pat. No. 5,653,863, such as ferrocyanide and ferricyanide. Examples of mediators also include electro-active organic molecules including coenzymes such as coenzyme pyrroloquinoline quinone (PQQ); the substituted benzoquinones and naphthoquinones disclosed in U.S. Pat. No. 4,746,607, which is incorporated herein by reference; the N-oxides, nitroso compounds, hydroxylamines and oxines specifically disclosed in EP 0 354 441, which is incorporated herein by reference; the flavins, phenazines, phenothiazines, indophenols, substituted 1,4-benzoquinones and indamines disclosed in EP 0 330 517, which is incorporated herein by reference; and the phenazinium and phenoxazinium salts disclosed in U.S. Pat. No. 3,791,988, which is incorporated herein by reference. A review of electrochemical mediators of biological redox systems can be found in *Analytica Clinica Acta.* 140 (1982), pages 1-18. Examples of electro-active organic molecule mediators also include those described in U.S. Pat. No. 5,520,786, which is incorporated herein by reference, including 3-phenylimino-3H-phenothiazine (PIPT), and 3-phenylimino-3H-phenoxazine (PIPO).

The second reagent layer 36 may include a soluble redox species. The soluble redox species undergoes the opposite redox reaction relative to the reaction of the analyte of the oxidoreductase, and in so doing is converted into its counterpart species of the redox pair. For example, if the analyte is reduced, the soluble redox species is oxidized; and if the analyte is oxidized, the soluble redox species is reduced. The counterpart species of the redox pair may also be present in the layer, but it is preferably present in a concentration lower than the concentration of the primary redox species. More preferably, the redox species in the reagent layer on the counter electrode is exclusively the soluble redox species that undergoes the opposite reaction relative to the reaction of the substrate of the oxidoreductase.

A soluble redox species may be an electro-active organic molecule, an organotransition metal complex, a transition metal coordination complex, or a combination thereof. Suitable electro-active organic molecules may include coenzyme pyrroloquinoline quinone (PQQ), substituted benzoquinones and naphthoquinones, N-oxides, nitroso compounds, hydroxylamines, oxines, flavins, phenazines, phenothiazines, indophenols, indamines, phenazinium salts, and phenoxazinium salts.

Suitable soluble redox species may also be OTM complexes or transition metal coordination complexes. Many transition metals occur naturally as compounds with hydrogen, oxygen, sulfur, or other transition metals, and these transition metals are generally observed in one or more oxidation states. For example iron, chromium, and cobalt are typically found in oxidation states of +2 (i.e. II) or +3 (i.e. III). Thus, iron (II) and iron (III) are two species of a redox pair. Many elemental metals or metal ions are only sparingly soluble in aqueous environments. This lack of solubility limits their utility as redox species in balancing the redox reactions in an electrochemical analysis system. The solubility of the otherwise sparingly soluble metals or metal ions may be improved through bonding or coordination with ligands.

Typically, the metal in an organotransition metal complex or a transition metal coordination complex is the moiety in the complex that is actually reduced or oxidized during use of the sensor strip. For example, the iron center in ferrocene [Fe(II)$(C_5H_6)_2$] and in the ferrocyanide ion [Fe(II)$(CN)_6$]$^{4-}$ is in the +2 formal oxidation state, while the ferricyanide ion [Fe(III)$(CN)_6$]$^{3-}$ contains iron in its +3 formal oxidation state. Together, ferrocyanide and ferricyanide together form a redox pair. Depending on the type of oxidoreductase present in the reagent layer of the working electrode, either metal complex can function as the soluble redox species in the reagent layer on the counter electrode. An example of a redox pair containing transition metal coordination complexes is the combination of two species of ruthenium hexaamine, [Ru(III)$(NH_3)_6$]$^{3+}$ and [Ru(II)$(NH_3)_6$]$^{2+}$.

The soluble redox species is capable of forming a redox pair during use of the electrochemical sensor strip. The species of this redox pair that is present in the reagent layer 36 on the counter electrode 30, referred to as the first species, is preferably present in a greater molar amount than its counterpart species (i.e. the second species) of the same redox pair. Preferably, the molar ratio of the first species to the second species is at least 1.2:1. More preferably, the molar ratio of the first species to the second species is at least 2:1. Still more preferably, the molar ratio of the first species to the second species is at least 10:1 or at least 100:1. In an aspect especially preferred at present, the second species of the redox pair is present in an amount of at most 1 part per thousand (ppt) or at most 1 part per million (ppm), prior to the use of the sensor strip in an analysis.

Preferably, the soluble redox species is solubilized in the sample and mixes with the analyte and other sample constituents. The soluble redox species will, over time, mix with the enzyme and the mediator, although this may not occur to any measurable degree over the course of the analysis. The soluble redox species is not separated from the liquid sample by a mechanical barrier, nor is it separate from the liquid sample by virtue of its existence in a separate phase that is distinct from the liquid sample.

In a preferred embodiment, a soluble redox species is chosen having a standard reduction potential of +0.24 volts or greater, versus the standard hydrogen electrode (SHE). In another preferred embodiment, a soluble redox species is chosen having a standard reduction potential of +0.35 volts or greater, versus SHE. In yet another preferred embodiment, a redox species having a reduction potential of about +0.48 volts versus SHE (in 0.01 M HCl) is chosen.

Thus, a wide variety of combinations of oxidoreductases, mediators, and soluble redox species can be used to prepare an electrochemical analytical sensor. The use of soluble redox species having higher or lower oxidation numbers relative to their counterpart species in the redox pair is dictated by the type of reaction to be performed at the working electrode.

In one example, the analyte undergoes oxidation by interaction with an oxidase or a dehydrogenase. In this case, the more concentrated redox species on the counter electrode has the higher oxidation number. A specific example of this situation is the analysis of glucose using glucose oxidase or glucose dehydrogenase. In another example, the analyte undergoes reduction by interaction with a reductase. In this case, the more concentrated redox species on the counter electrode has the lower oxidation number. In either of these examples, the mediator may be the same substance as the more concentrated redox species on the counter electrode or the redox species of another redox pair.

Figure 3:
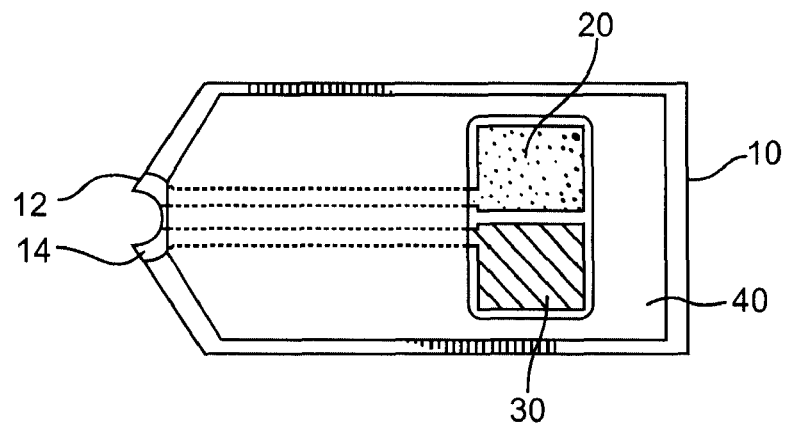
FIG. 3 is a top view diagram of a sensor base and electrodes under a dielectric layer.

FIG. 3 is a top view diagram of the sensor base 10, including the conductors 12 and 14 under a dielectric layer 40, and the electrodes 20 and 30. The dielectric layer 40 may partially cover the electrodes 20 and 30 and may be made from any suitable dielectric layer, such as an insulating polymer. The dielectric layer 40 may isolate the portions of the electrodes that are in contact with the first and second reagent layers 26 and 36 from the portions of the electrodes that are in contact with the conductors 12 and 14. The dielectric layer 40, if present, may be deposited on the sensor base 10 before, during, or after the coating of the electrodes 20 and 30 with the reagent layers 26 and 36, respectively.

The electrodes 20, 30 may be coated with the reagent layers 26, 36 by any convenient means, such as printing, liquid deposition, or ink-jet deposition. In one aspect, the reagent layer is deposited on the electrodes 20, 30 by printing. With other factors being equal, the angle of the printing blade may inversely affect the thickness of the reagent layer residing on the electrodes 20, 30. For example, when the blade is moved at an approximately 82° angle to the sensor base 10, the resulting reagent layer or layers may have a thickness of approximately 10 μm. Similarly, when a blade angle of approximately 62° to the sensor base 10 is utilized, a thicker 30 μm layer may be produced. In this aspect, lower blade angles may provide thicker reagent layers. In addition to blade angle, other factors affect the resulting thickness of the reagent layers 26, 36, including the thickness of the material making up the reagent layer.

Figure 4:
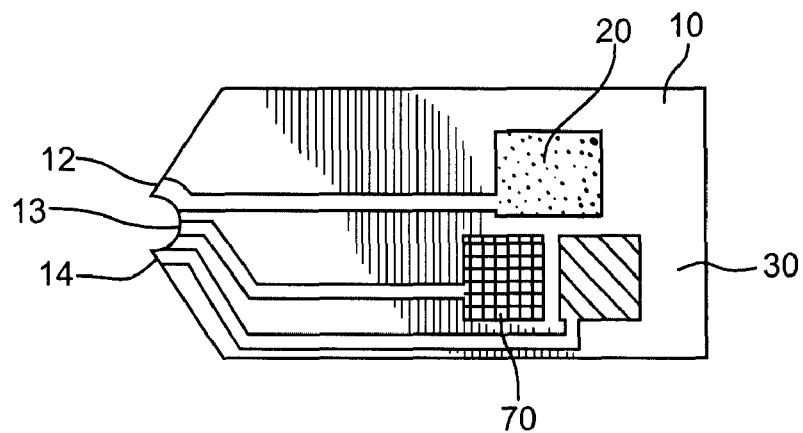
FIGS. 4-6 are top views of three electrode sensor strips.
Figure 5:
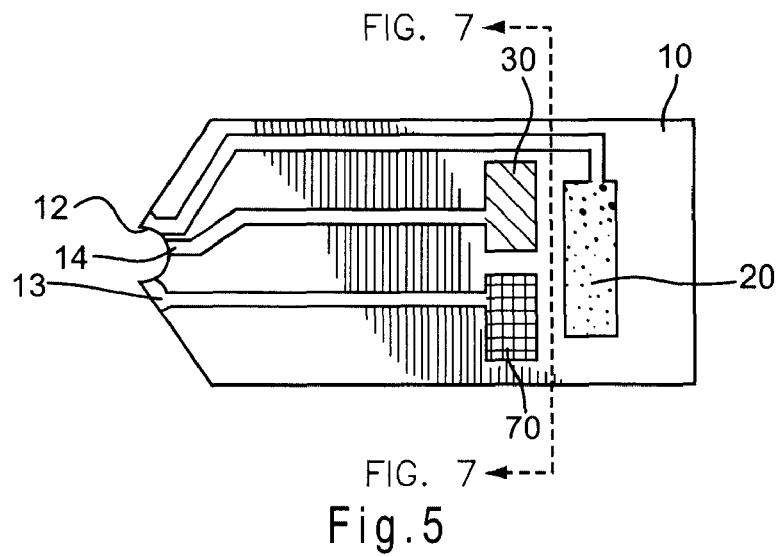
Figure 6:
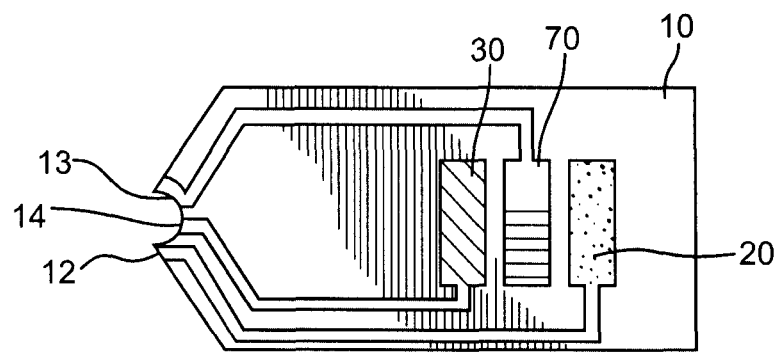

FIGS. 4-6 are top views of three electrode sensor strips, each having the sensor base 10, the working electrode 20, the counter electrode 30, the conductors 12 and 14, a conductor 13, and a third electrode 70. The third electrode 70 may be in electrical communication with the measurement device (not shown) through the conductor 13.

The measurement device may measure an electric potential flowing between the working electrode 20, the third electrode 70, and a sample (not shown) that establishes electrical communication between the electrodes. In another aspect, the measurement device may apply and measure an electrical potential provided to the working electrode 20, the third electrode 70, and the sample. The sensor base 10 may have other configurations including those with fewer or additional components as is known in the art.

Figure 7:
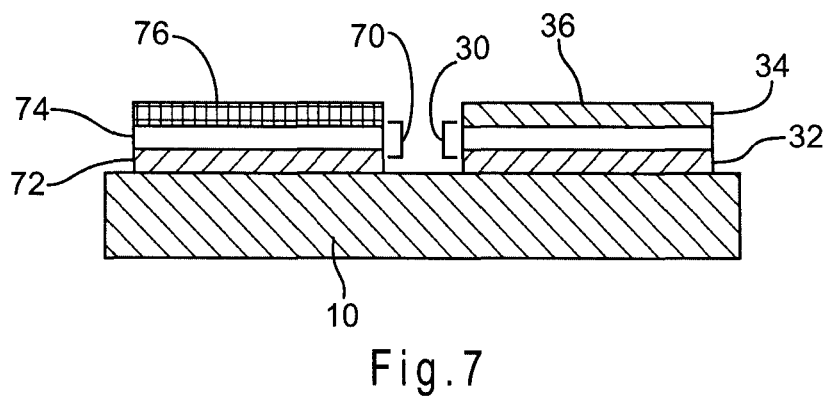
FIG. 7 is an end view diagram of the sensor base of FIG. 5 depicting the third electrode.

FIG. 7 is an end view diagram of the sensor base 10 of FIG. 5 depicting the optional third electrode 70. In one aspect, the optional third electrode 70 may be a true reference electrode.

In another aspect, the third electrode 70 may be coated with a third reagent layer 76 including a soluble redox species. An optional third electrode surface conductor 74 may reside on a third main conductor 72. In one aspect, the third main conductor 72 includes metal foil while the surface conductor 74 includes one or more layers of conductive carbon powder. The third reagent layer 76 and the second reagent layer 36 may include the same constituents or have different constituents depending on the intended use. In one aspect, the third reagent layer 76 is a portion of the second reagent layer 36, which is deposited on the main conductors 32 and 72.

When the surface conductor 74 is deposited on the main conductor 72, it is preferred that the substance from which the surface conductor is made is a non-ionizing conductive material. When the main conductor 72 is utilized without the distinct surface conductor layer 74, it is preferred that the conductive material from which the main conductor is made is non-ionizing. More preferably, the portion of the third electrode 70 in contact with the third reagent layer 76 (either the main conductor 72 or the surface conductor 74) is a non-ionizing material. The third reagent layer 76 may include the same constituents as the first and second reagent layers 26 (not shown) and 36. In another aspect, the third reagent layer 76 may include the same constituents as the second reagent layer 36. In yet another aspect, the third reagent layer 76 may include ingredients that are specifically tailored to improve the free flow of electrons between the sample being analyzed and the third main conductor 72.

The reagent layer 76 may contain a soluble redox species as described above with regard to FIG. 2. Preferably the reagent layer 76 of the third electrode 70 is identical in composition to the reagent layer 36 of the counter electrode 30. If the reagent layers on the third and counter electrodes are identical, then it may be desirable to coat both electrodes with a single portion of the reagent layer composition.

The use of the third electrode 70 may be desirable for some applications. Increased accuracy in the applied voltage can provide for better accuracy in the measurement of the analyte. When using the third electrode 70, it may also be possible to reduce the size of the counter electrode 30 or to apply a smaller amount of the redox species to the counter electrode. If the third electrode 70 is positioned upstream of the counter electrode 30, as illustrated in FIG. 6, then it may be possible to detect when insufficient sample has been applied to the strip, a situation referred to as "under-fill." Under-fill detection may occur when there is sufficient sample to complete the circuit between the working electrode 20 and the third electrode 70, but not to cover the counter electrode 30. The lack of electrical current in the cell can be converted electronically into a signal to the user, instructing the user to add additional sample to the strip.

Figure 8:
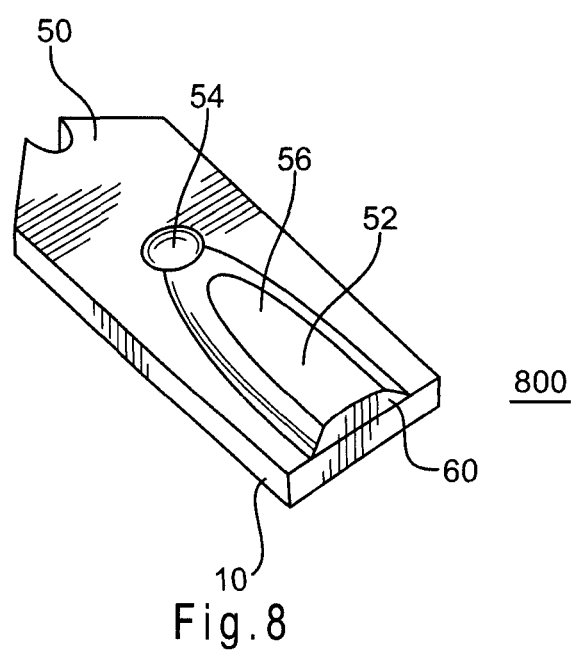
FIG. 8 is a perspective representation of a completely assembled sensor strip.

FIG. 8 is a perspective representation of an assembled sensor strip 800 including the sensor base 10, at least partially covered by a lid 50 that includes a vent 54, a concave area 52, and an input end opening 60. Preferably, the lid 50 covers, but does not contact, the reagent layers 26 and 36 (not shown), thus providing a gap 56 between the lid 50 and the electrodes.

A biological sample may be transferred to the electrodes by introducing the liquid sample to the opening 60 of the sensor strip 800. The liquid fills the gap 56 while expelling the air previously contained by the gap 56 through the vent 54. In this manner, the sample provides electrical communication between the electrodes. The gap 56 may contain a substance (not shown) that assists in retaining the liquid sample in the gap by immobilizing the sample and its contents in the area above the electrodes. Examples of such substances include water-swellable polymers, such as carboxymethyl cellulose and polyethylene glycol; and porous polymer matrices, such as dextran and polyacrylamide.

If a sample introduced through the opening 60 contains an analyte for the oxidoreductase, the redox reaction between the analyte and the enzyme can begin once the reagent layers and the sample are in contact. The electrons produced or consumed from the resultant redox reaction can be quantified by applying an electrical potential (i.e. voltage) between the working electrode and the counter electrode, and measuring the current. This current measurement may be correlated with the concentration of the analyte in the sample, provided the system has been calibrated with similar samples containing known amounts of the analyte.

Alternatively, the third electrode 70 (FIGS. 4-7) may be used to monitor the applied voltage. Any drift in the intended value of the electrical potential may provide feedback to the circuitry through the third electrode, so that the voltage can be adjusted appropriately. A measurement device preferably contains the necessary circuitry and microprocessors to provide useful information, such as the concentration of the analyte in the sample, the concentration of the analyte in the body of the patient, or the relevant concentration of another substance that is related to the measured analyte.

Once the sample is introduced through the opening 60, the sample begins to solubilize and react with the reagent layers 26, 36, and optionally 76. It may be beneficial to provide an "incubation period" during which the reagents convert a portion of the analyte into a measurable species prior to the application of an electrical potential. While a longer incubation period may be utilized, preferably, a voltage is initially applied to the sensor strip 800 at the same time as, or immediately after, the introduction of the sample through the opening 60. A more in-depth treatment of incubation periods may be found in U.S. Pat. Nos. 5,620,579 and 5,653,863.

The initially applied voltage may be maintained for a set time period, such as about 10 seconds for a conventional sensor strip, and then stopped. Then no voltage may be applied for a set delay time period, such as about 10 seconds for a conventional sensor strip. After this delay time, a constant potential or a "read pulse" may be applied across the working and counter electrodes of the sensor strip to measure the concentration of the analyte. For conventional amperometric sensors, this read pulse is applied while the current is monitored for a read time of from 5 to 10 seconds. Considering the sample volume contained by the gap 56, a read pulse of from 5 to 10 seconds is relatively long.

In contrast to the conventional 5 to 10 second read pulse, when the working electrode 20 (FIG. 2) is configured with the DBL of the present invention, shorter read times are preferred. FIGS. 9A and 9B depict a working electrode 900 having a conductor surface 930 and a DBL 905 during the application of long and short read pulses. A sample (not shown) is applied to the working electrode 900 and includes RBC 920 residing on the DBL 905, external measurable species 910 residing in the sample, and internal measurable species 915 residing within the DBL 905.

As shown in FIG. 9A, when a long, 10 second read pulse is applied to the working electrode 900, both the external and internal measurable species 910 and 915 are measured at the surface of the conductor surface 930 by a change in oxidation state. During this measurement process, the external measurable species 910 diffuses through the sample region where the RBC 920 reside and through the DBL 905 to be measured at the surface 930. As previously discussed, this diffusion of the external measurable species 910 through the RBC 920 during measurement introduces the hematocrit effect.

Furthermore, a long read pulse applied to a strip having a DBL, as depicted in FIG. 9a, performs similarly to a short read pulse applied to a strip lacking a DBL. The similarity arises because measurable species diffuse through the RBC before being measured at the conductor surface during the read pulse. In either instance, a substantial portion of the species measured during the read pulse originated in the test sample.

Unlike FIG. 9A, FIG. 9B represents the situation where a short read pulse is applied to the sensor strip 900 having the DBL 905 in accord with the present invention. Here, the internal measurable species 915 present in the DBL 905 undergoes a change in oxidation state at the surface 930. Substantially all of the measurable species 910 residing external to the DBL 905 either remains external to the DBL or does not substantially diffuse through the DBL 905 to reach the conductor surface 930 during the read pulse. Thus, the present invention substantially excludes the external measurable species 910 from measurement, instead measuring the measurable species 915 that is internal to the DBL 905.

Figure 10A:
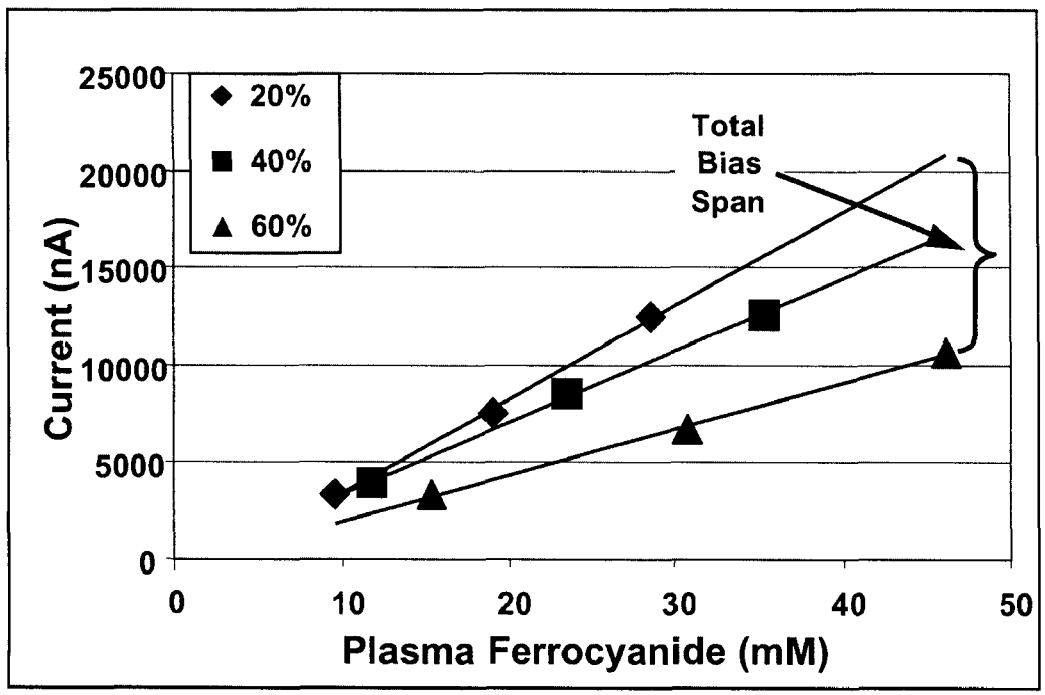
FIGS. 10A and 10B are graphs illustrating the improvement in measurement accuracy when a DBL is combined with a short read pulse in accord with the present invention.
Figure 10B:
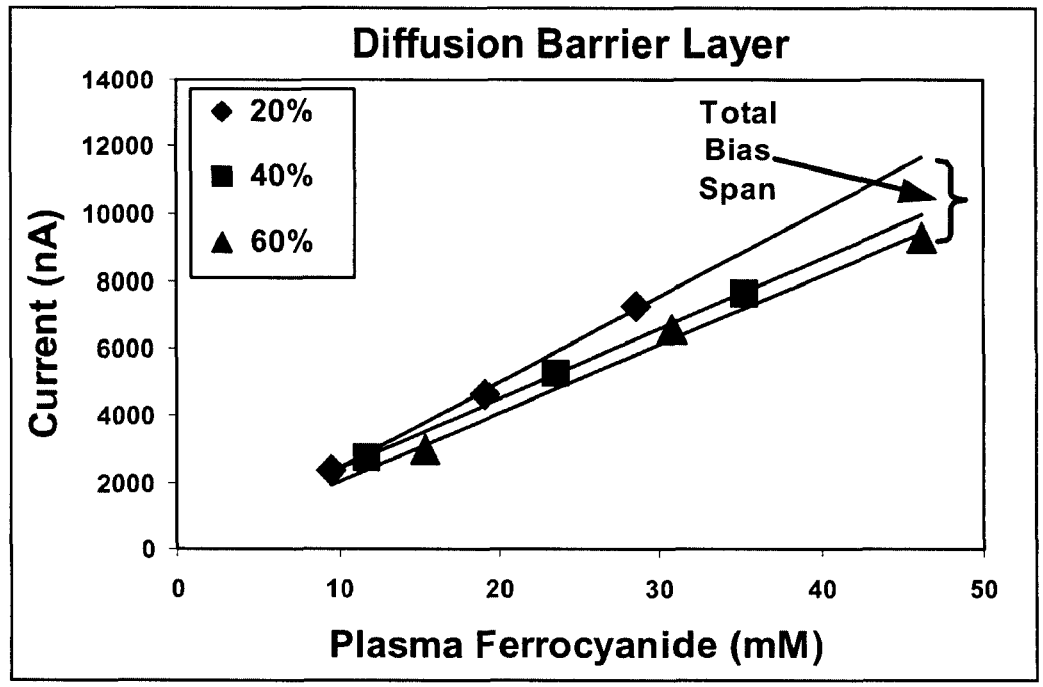

FIGS. 10A and 10B are graphs illustrating the improvement in measurement accuracy when a DBL is combined with a short read pulse in accord with the present invention. Whole blood samples were combined with ferrocyanide in a 5:1 dilution ratio to represent an underlying glucose concentration and measured with a 1 second read pulse. Thus, the initial 20%, 40% and 60% hematocrit WB samples were diluted to 16%, 32% and 48% hematocrit (a 20% reduction of all three hematocrit values). The 20%, 40%, and 60% lines represent the current measured for the blood samples containing 16%, 32%, and 48% hematocrit, respectively.

FIG. 10A shows the inaccuracies introduced by the hematocrit and other effects from a bare conductor sensor strip lacking a DBL. The inaccuracy is represented as the difference between the 20% and 60% hematocrit lines (the total hematocrit bias span) and represents the maximum measurement inaccuracy attributable to the hematocrit effect. Smaller bias values represent a more accurate result. Similar performance was observed when a DBL was used with a longer read pulse as discussed above with regard to FIG. 9A.

Conversely, FIG. 10B shows a marked decrease in the distance between the 20% and 60% calibration lines when a DBL in accordance with the present invention is combined with a 1 second read pulse. A distinct DBL of PEO polymer and 10% KCl (without reagents) was printed on a conductor surface as used for FIG. 10A above. Surprisingly, the total bias hematocrit span with the DBL/short read pulse was nearly two-thirds less than the total bias span without the DBL. Thus, the present invention significantly increased measurement accuracy in comparison to the conventional, bare conductor electrode.

While not wishing to be bound by any particular theory, it is presently believed that by limiting the length of the read time with respect to the thickness of the DBL, the present invention may exploit the phenomenon that the rate of diffusion of the measurable species into the pores of the DBL is varying, while the diffusion rate of the measurable species from the internal volume of the DBL to the surface of the conductor surface is constant. The varying degree of diffusion into the DBL caused by the WB matrix is believed to give rise to the hematocrit effect. Thus, measurement errors (bias) introduced by the sample constituents, including RBC, may be reduced by substantially limiting measurement to the measurable species present in the internal volume of the DBL, which are believed to have a relatively constant diffusion rate.

Figure 11A:
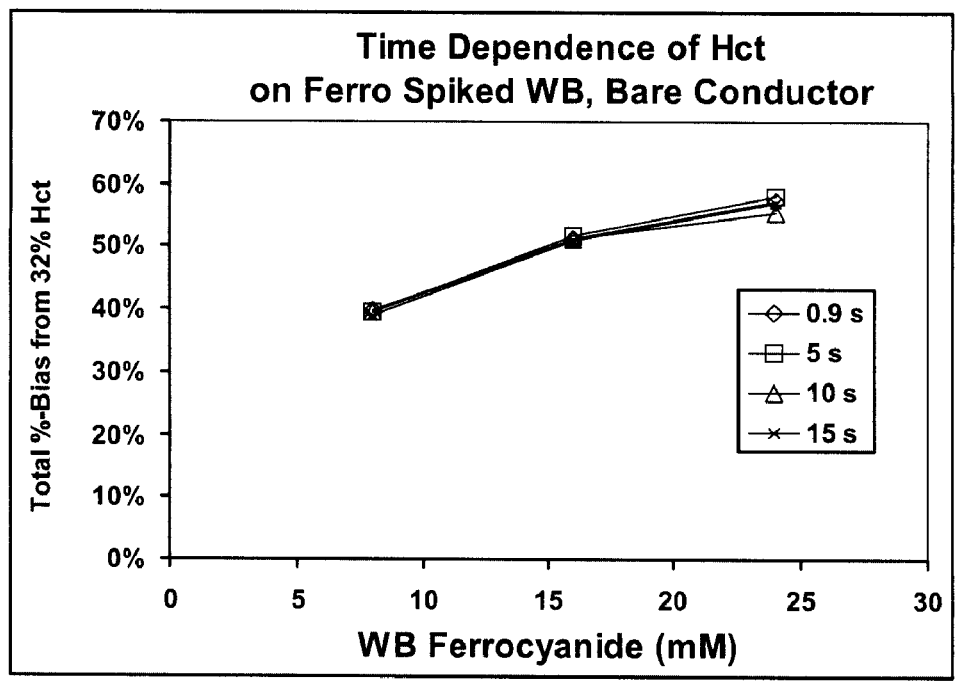
FIGS. 11A and 11B are graphs establishing the improvement in accuracy arising from a reduction in the duration of the read pulse when a DBL is utilized.
Figure 11B:
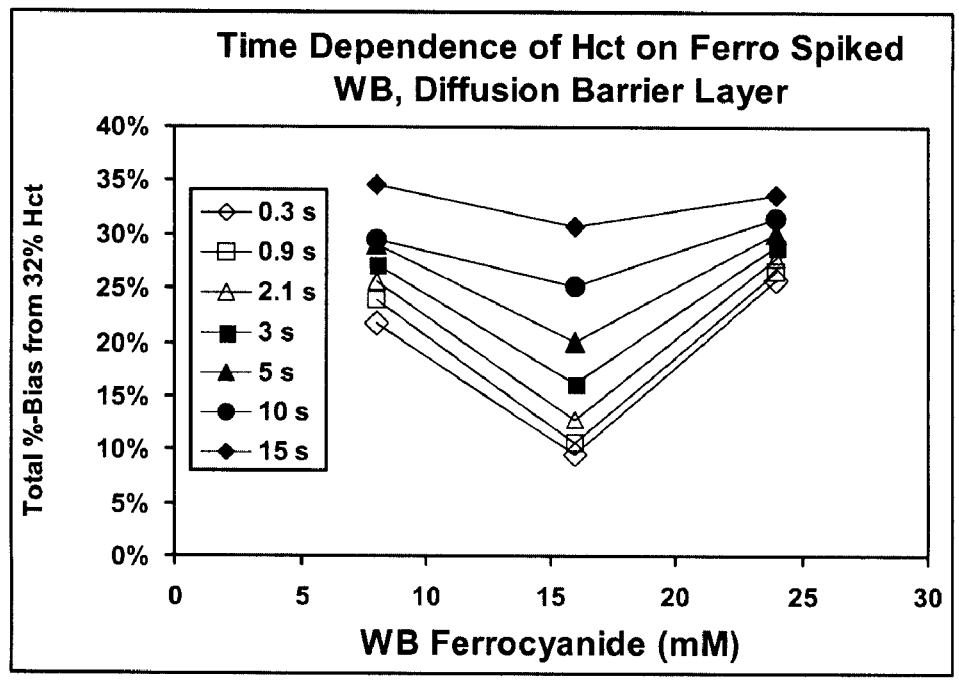

FIGS. 11A and 11B are graphs establishing the improvement in accuracy arising from a reduction in the duration of the read pulse when a DBL is utilized. FIG. 11A shows that without a DBL, the bias with read pulses of 0.9, 5, 10, and 15 seconds are nearly identical. Regardless of the length of the read pulse, the total bias span values are 40% and higher (50% on average), because the ability of the mediator to reach the surface of the conductor is affected by the sample constituents, including RBC. However, as illustrated in FIG. 11B, when a DBL is utilized, the bias for the 0.9 second read pulse is generally less than half of the bias observed for the 5 second read pulse and can be as much as 2.5 times less than the bias observed for a conventional 10 second read pulse, depending on the ferrocyanide concentration.

When combined with a DBL, read pulses of less than 5 seconds are preferred and read pulses of less than 3 seconds are more preferred. In another aspect, read pulses from 0.1 to 2.8 or from 0.5 to 2.4 seconds are preferred. In yet another aspect, read pulses from 0.05 to 2.8 or from 0.1 to 2.0 seconds are preferred. At present, read pulses from 0.8 to 2.2 or from 0.8 to 1.2 seconds are more preferred, while read pulses from 0.1 to 1.5 or from 0.125 to 0.8 seconds are especially preferred. The thickness of the DBL present during application of the read pulse may be selected so that during the pulse, the measurable species external to the DBL is substantially prevented from diffusing to the surface of the conductor.

FIG. 12 is a table comparing the bias results for 1 and 10 second read pulses from multiple analyses performed with multiple types of sensor strips having a DBL. The table shows the total bias span values for WB samples containing 50, 100, 200, and 400 mg/dL glucose. Absolute bias values are listed for the 50 mg/dL samples, while % bias is shown for the 100, 200, and 400 mg/dL samples. The bias values for the varying glucose concentrations were averaged for both the 10 second and the 1 second read pulses. The shorter 1 second read pulse provided a substantial reduction in the bias values when compared with the conventional 10 second read pulse, with reductions from about 21% to about 90%. For the 36 trials performed, the overall average bias reduction was about 50%. Thus, the combination of a DBL with a short read pulse in accord with the present invention significantly increased measurement accuracy.

Figure 13A:
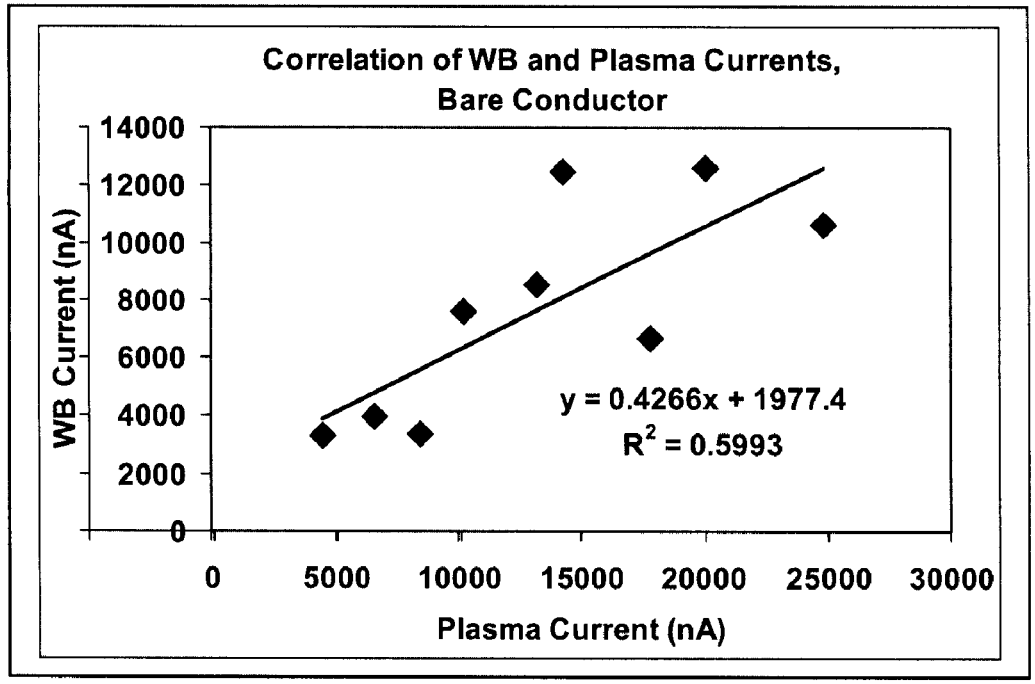
FIGS. 13A-13C are graphs illustrating the ability of a sensor strip having a DBL in accordance with the present invention to accurately measure the true glucose concentration of a sample utilizing a short read pulse.
Figure 13B:
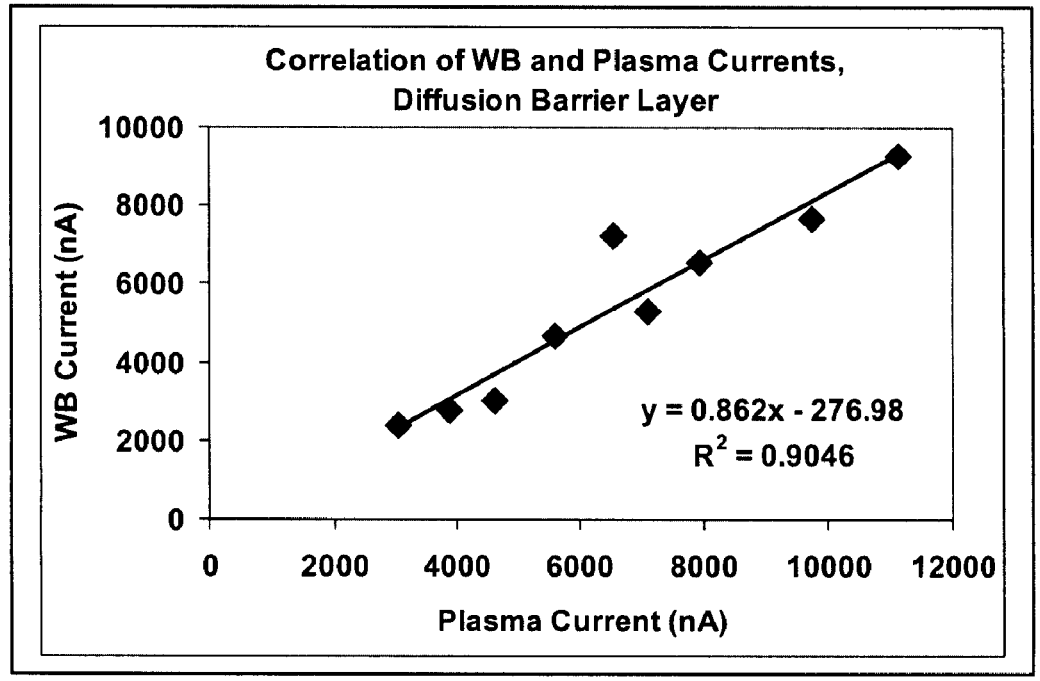
Figure 13C:
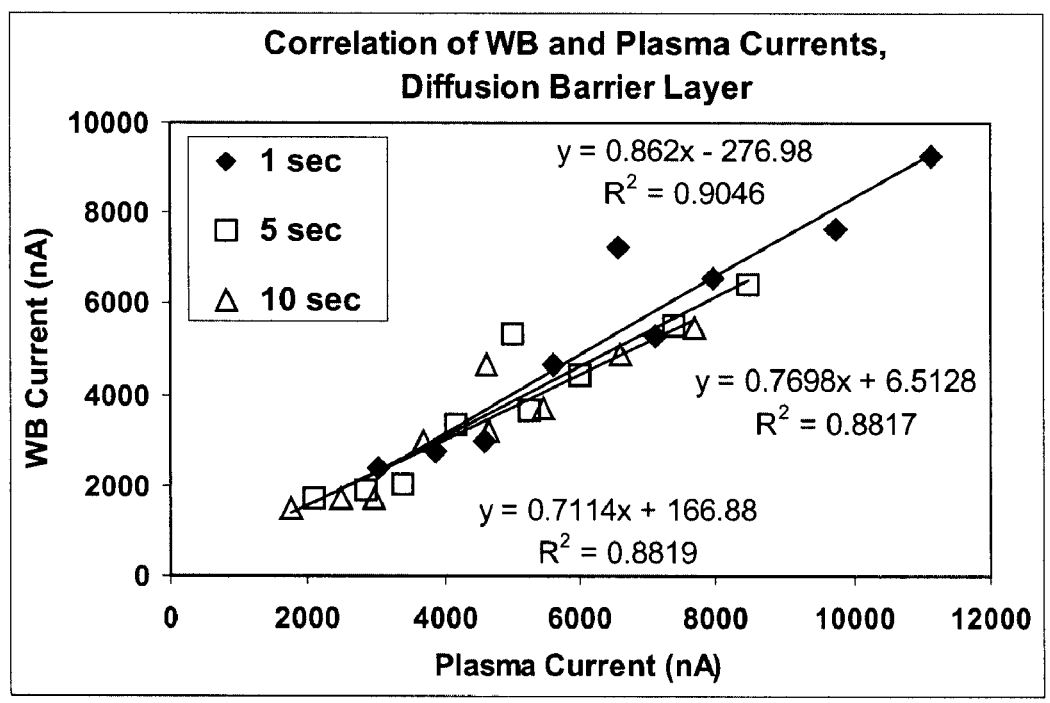

FIGS. 13A-13C are graphs illustrating the ability of a sensor strip having a DBL to accurately measure the true glucose concentration of a sample utilizing a short read pulse. The data underlying the figures was collected by measuring the current in WB and plasma solutions containing ferrocyanide as the measurable species. Because the plasma samples lack RBC, the plasma measurements lack inaccuracies introduced by the hematocrit effect. Conversely, measurements taken in the WB samples included inaccuracies introduced by the hematocrit effect.

FIG. 13A correlates plasma and WB measurements collected with a 1 second read pulse for a bare conductor sensor strip. The slope of the resulting correlation plot is only 0.43, indicating that on average only 43% of the measurable species present in the WB samples was measured. In comparison, FIG. 13B correlates plasma and WB measurements collected with a 1 second read pulse for a sensor strip having a DBL. The slope of the resulting correlation plot is a substantially higher 0.86, indicating that about 86% of the measurable species present in the WB samples was measured. Thus, when compared with a bare conductor, a short read pulse combined with a DBL in accordance with the present invention may provide a 100% improvement in the measured versus actual analyte concentration in WB samples.

FIG. 13C illustrates that decreased duration read pulses enhance measurement performance for sensor strips equipped with a DBL in accord with the present invention. The graph shows the correlation plots for 1, 5, and 10 second read pulse measurements taken in the WB and plasma samples previously described with respect to FIGS. 13A and 13B. The 1, 5, and 10 second pulses have correlation plot slopes of 0.86, 0.78 and 0.71, respectively. Thus, decreases in read pulse duration reduced measurement inaccuracies.

When a combination DBL/reagent layer is used, the length of the initial pulse and the delay affect the thickness of the DBL during the later applied read pulse. As previously discussed, combination DBL/reagent layers rely on a water soluble binder material that is partially solubilized into the sample prior to application of the read pulse. The reagent containing binder material remaining during the read pulse serves as the DBL.

Because solubilization of the binder material begins as soon as the sample is introduced through the opening 60 (FIG. 8), the time that passes during the initial pulse and delay periods affects how much of the combined layer remains on the conductor surface during the read pulse. Thus, shorter initial pulses and delay times may be preferred to ensure that sufficient binder material remains on the conductor to serve as an effective DBL.

However, depending on the duration of the read pulse, a preferable upper limit exists for the DBL thickness because an increased DBL thickness may result in a failure of the sensor system to reach "steady-state" before application of the read pulse. Before the sensor system reaches steady-state, the concentration of the measurable species in the DBL does not accurately represent the concentration of the measurable species in the sample. In one aspect, this discrepancy between the concentrations of the measurable species in the DBL and the sample may be attributed to the changing rehydration state of the DBL.

Thus, if read pulses are applied and recorded before the steady-state condition is reached, the concentration of the measurable species measured may not correlate with that in the sample. This lack of correlation between the measurable species concentration in the DBL and the sample may introduce inaccuracies into the measurement, thereby offsetting the accuracy improvement otherwise obtained by excluding the measurable species external to the DBL from measurement.

FIGS. 14A through 14F present the results obtained for multiple glucose concentrations when different initial thicknesses of a combination DBL/reagent layer were utilized with sequential 1 sec read pulses. The data was obtained utilizing multiple 200 mV read pulses, each of 1 second duration, separated by 0.5 second waits. Table II below lists the approximate average DBL/reagent layer thickness and the approximate time to reach steady state for each figure. The approximate beginning of the steady-state condition may be observed when the last in time data point obtained for an individual read pulse represents the greatest current value of the last in time data points acquired for any individual read pulse.

Figure 14A:
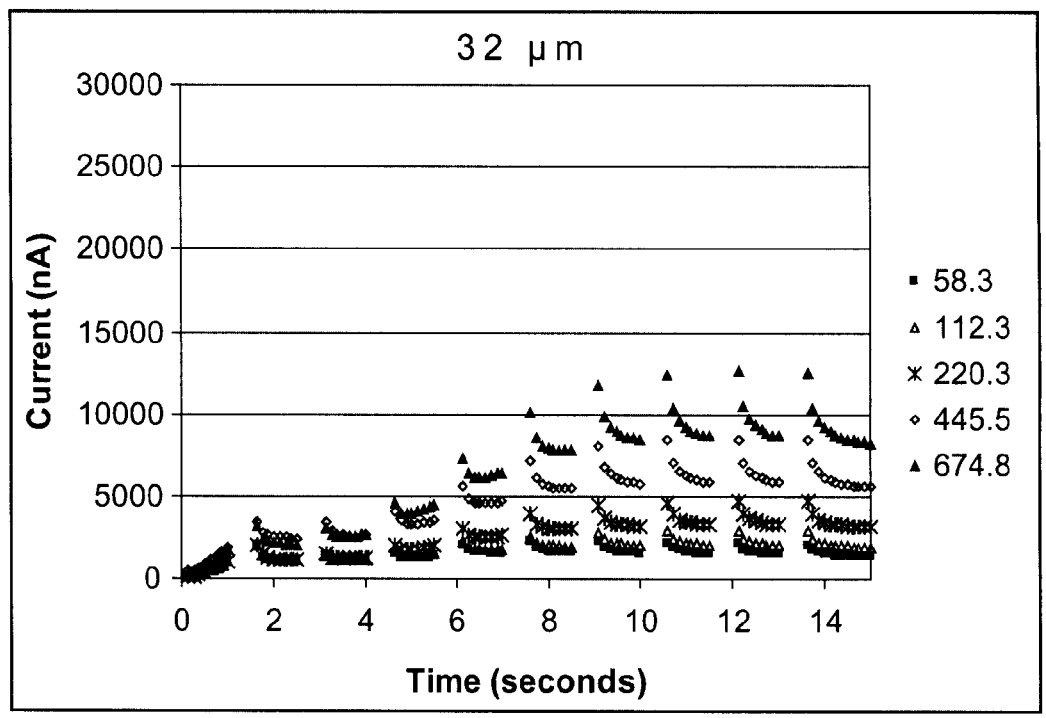
FIGS. 14A-14F are graphs illustrating the decay profiles for multiple glucose concentrations when different thicknesses of a combination DBL/reagent layer were utilized with sequential 1 sec read pulses.
Figure 14B:
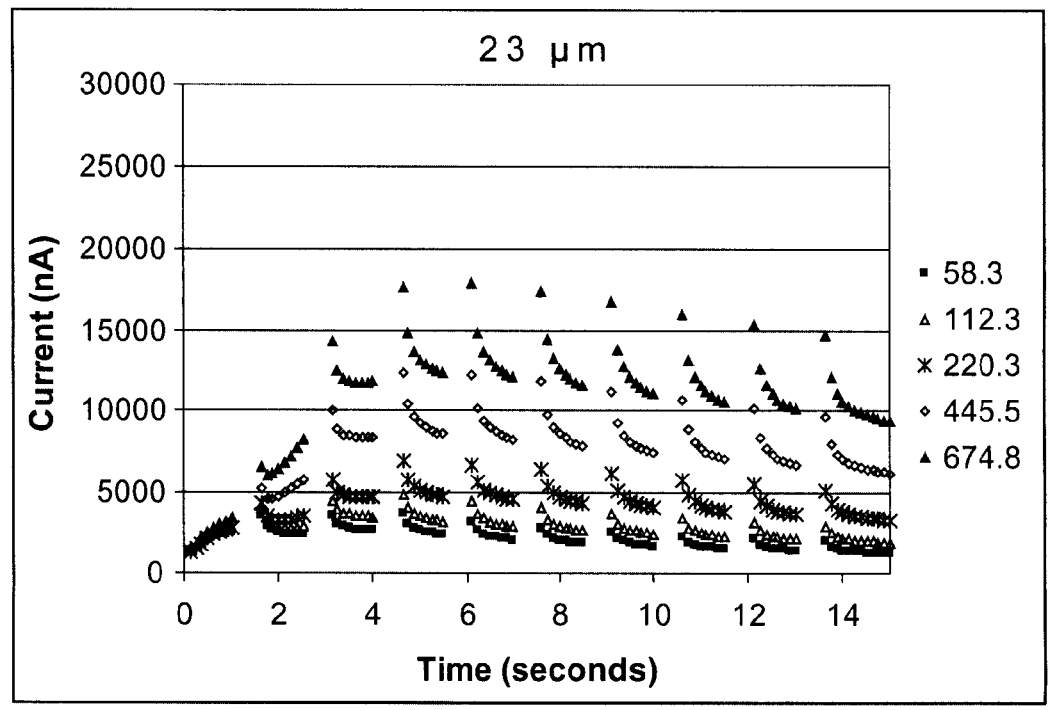
Figure 14C:
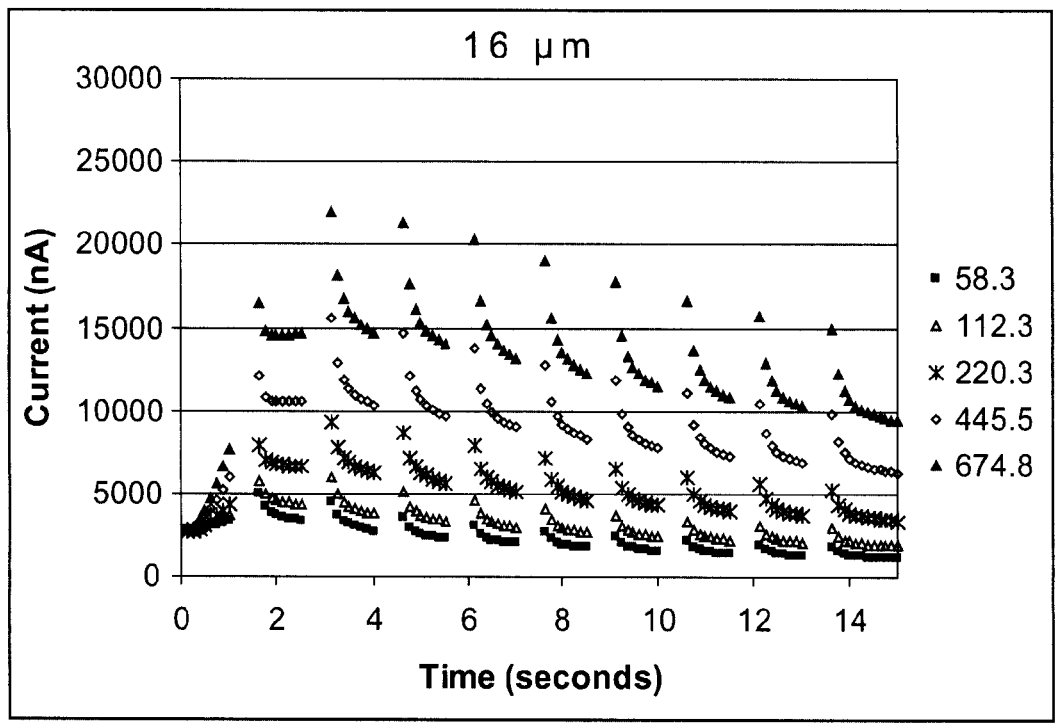
Figure 14D:
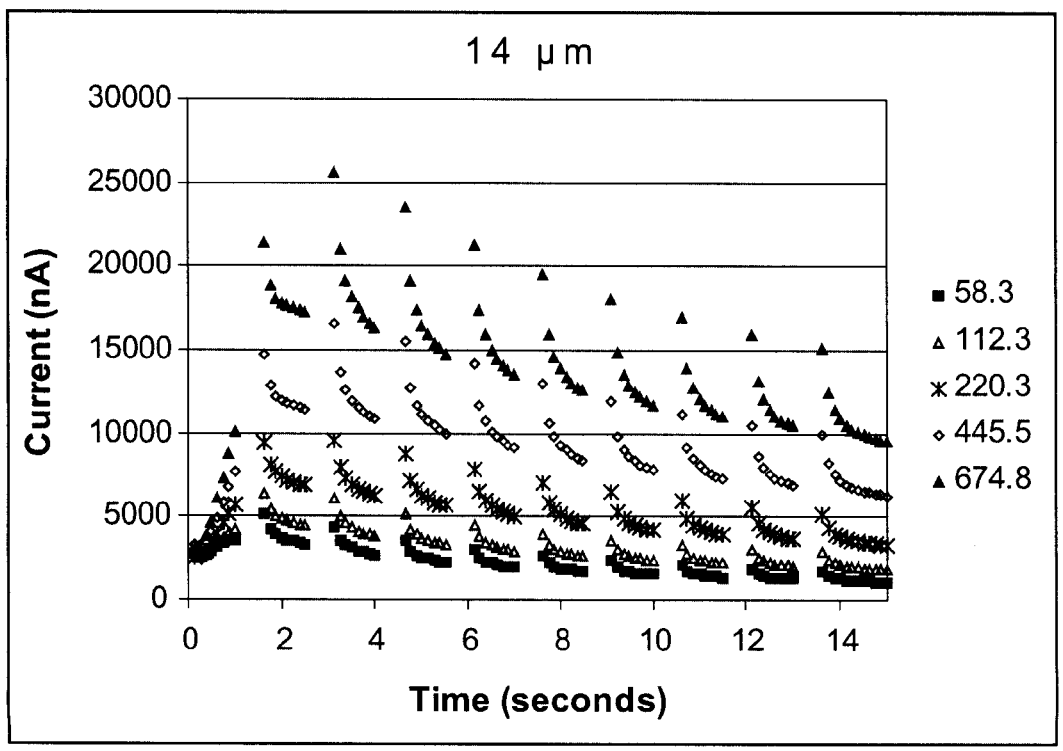
Figure 14E:
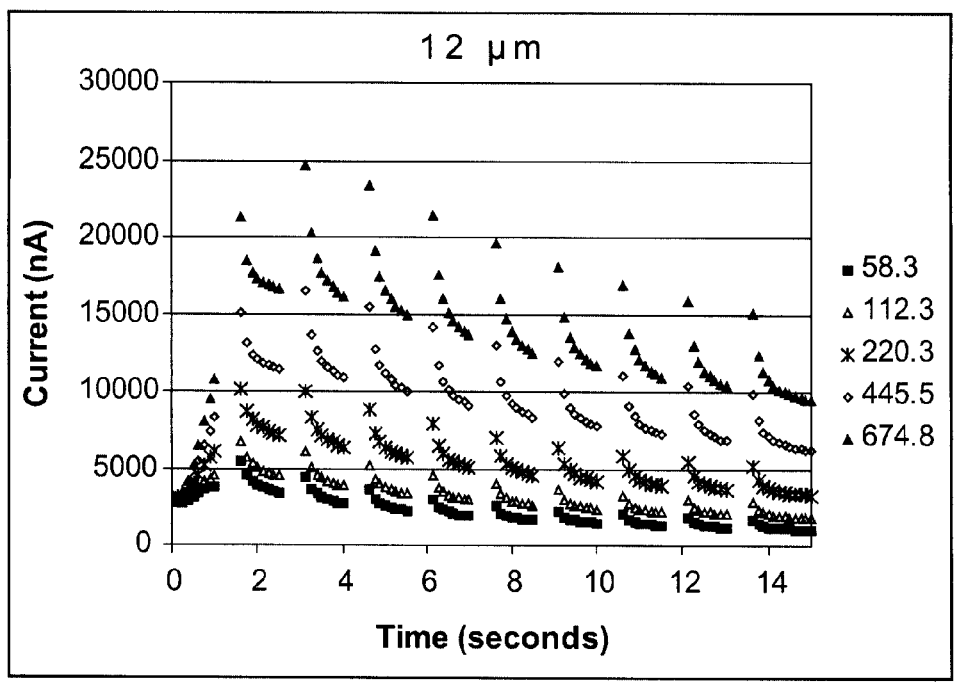
Figure 14F:
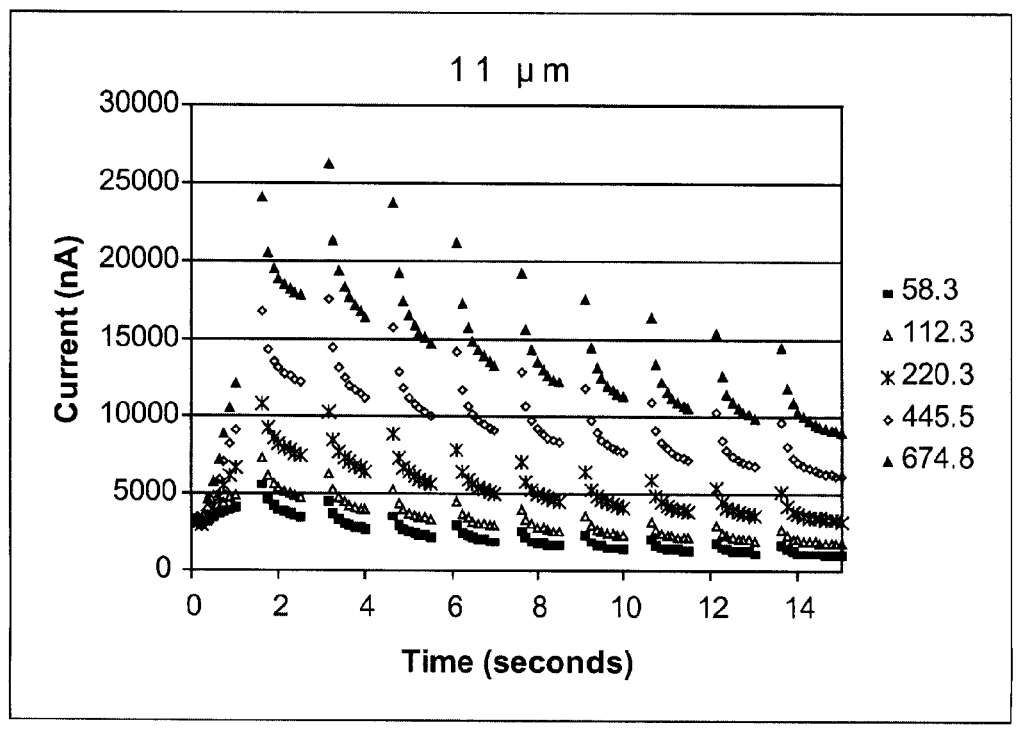
Figure 14G:
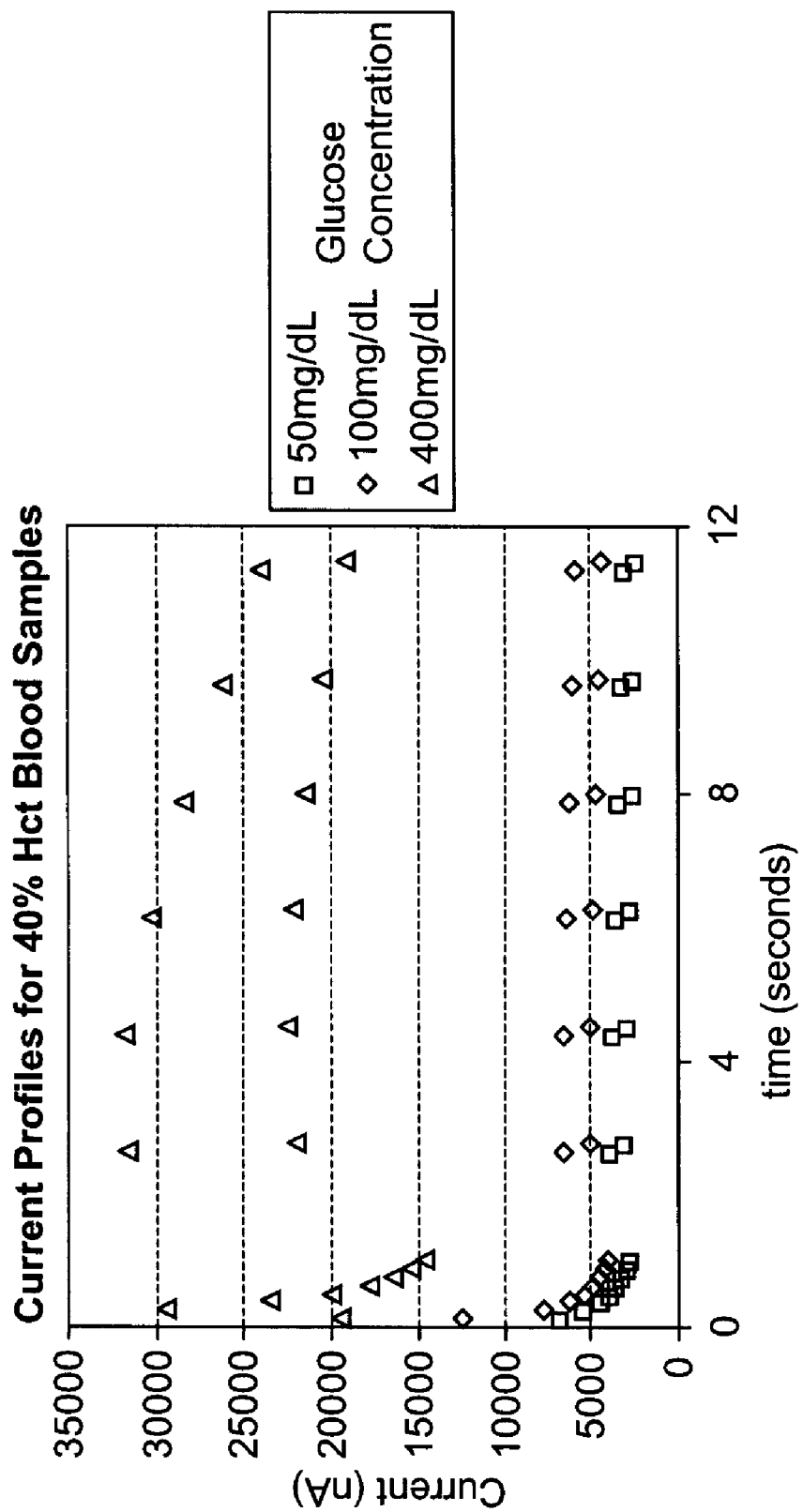
FIG. 14G illustrates the decay profiles for multiple glucose concentrations for a 1 to 2 μm combined DBL/reagent layer with an initial 1 second pulse followed by sequential 0.25 second read pulses.

Thus, for FIG. 14F, the last in time (rightmost) ~1750 nA data point for the read pulse initiated at ~1.5 seconds establishes that steady-state was reached at about 2.5 seconds at the 674.8 mg/dL glucose concentration.

TABLE II

| FIG. | Approximate DBL/reagent layer average thickness in μm. | Approximate time to reach steady state in seconds. |
| --- | --- | --- |
| 14A | 30 | >10 |
| 14B | 23 | 5.5 |
| 14C | 16 | 4 |
| 14D | 14 | 2.5 |
| 14E | 12 | 2.5 |
| 14F | 11 | 2.5 |
| 14G | 1 to 2 | 1 |

The data in Table II establish that for a 1 second read pulse preceded by a 0.5 second delay, the average initial thickness of a combination DBL/reagent layer is preferably less than 30 or 23 micrometers (μm) and more preferably less than 16 μm. Preferred average initial thicknesses of a combination DBL/reagent layer for use with a 0.5 to 5 second delay and a 0.5 to 1.2 second read pulse are from 5 to 15 μm or from 11 to 14 μm. More preferred average initial thicknesses of a combination DBL/reagent layer for use with a 0.5 to 5 second delay and a 0.05 to 2.8 second read pulse are from 1 to 15 μm or from 2 to 5 μm. Thus, for a 0.8 to 1.2 second read pulse, these thicknesses substantially exclude measurable species external to the DBL from the conductor surface during the read pulse, while allowing the sensor system to reach a steady-state.

While the preferred initial thickness of the reagent layer applied to the conductor is dependent on the initial pulse length, the delay time, and the duration of the read pulse, for read pulse durations of less than five seconds, reagent layer thicknesses of from 5 to 30 μm or from 11 to 20 μm are preferred. Furthermore, for read pulses of 1.5 seconds or less in duration, reagent layer thicknesses of from 1 to 10 μm or from 2 to 5 μm are preferred. The desired average initial thickness of a combination DBL/reagent layer may be selected for a specific read pulse length, such as for the 1 second read pulse of Table II, on the basis of when steady-state is reached.

In one aspect, initial pulse and delay times of less than 6 seconds are preferred. Initial pulse times of from 1 to 4 seconds and delay times of from 0.5 to 5 seconds are more preferred. In a preferred aspect, the initial pulse and delay times are selected so that at least 50% of the average initial thickness of the combined DBL/reagent layer remains on the conductor surface when the read pulse is applied. In another aspect, from 60 to 85% or from 70 to 80% of the average initial thickness of the combined layer remains on the conductor surface when the read pulse is applied.

The preferred thickness of the DBL for a specific read pulse length also may depend on the nature of the DBL. The slower the measurable species moves through the DBL during measurement, the thinner the DBL required. However, if diffusion of the measurable species through the DBL is too slow, it may be difficult to obtain the desired steady-state condition. The rate at which a measurable species diffuses through the DBL also may be altered with additives that affect the ionic strength of the test sample and/or of the pore interiors of the DBL. In one aspect, the additive may be a salt, such as sodium or potassium chloride, which is present in the deposition solution/paste at a 1 to 2 Molar concentration. Other salts and compositions that affect the ionic strength of the test sample as known to those of ordinary skill in the art of chemistry also may be used.

Another advantage of measuring the measurable species in the DBL with a less than 3 second read pulse is the reduction of measurement imprecision from varying sample volumes present in the gap 56 of the sensor strip 800 (FIG. 8). If a read pulse continues past the time when substantially all of the measurable species present in the gap 56 has been measured, the measurement no longer represents the concentration of measurable species in the sample, but is instead measuring the amount of measurable species in the gap 56; a very different measurement. As the read pulse becomes long relative the volume of the gap 56, the current measurement will depend on the volume of the gap 56, not the underlying analyte concentration. Thus, longer read pulses can result in measurements that are highly inaccurate with regard to analyte concentration if the pulse length "overshoots" the measurable species present in the gap 56.

Hence, any variance in the volume of the gap 56 present in the electrochemical sensor strip may lead to measurement imprecision because the electronics in the measurement device apply the same potential and perform the same calculations for each test. Thus, for the same sample, a conventional sensor strip having a larger gap volume will show a higher analyte concentration than a sensor strip having a smaller gap volume if the read pulse overshoots the gap volume. By substantially limiting measurement to the measurable species present in the DBL, the present invention may reduce the imprecision introduced by sensor strips having different gap volumes. In this manner, the effect that manufacturing variability in the sensor strips would otherwise have on the measurement results may be reduced.

FIG. 15 compares the precision between sensor strips having a DBL and gap volumes of 1, 3, 5, and 10 μL when read pulses of 1, 5, 10, and 15 seconds were applied. Table A presents the data collected when a 2 second pre-pulse and a 4 second delay was followed by read pulses of 1, 5, 10, and 15 seconds. Table B presents the data collected when a 4 second pre-pulse and a 2 second delay was followed by read pulses of 1, 5, 10, and 15 seconds. Variances between slopes and intercepts of the calibration lines for each combination of gap volume and read pulse duration are expressed as %-CV. The %-CV values from tables A and B show that as the duration of the read pulse increases so does the imprecision in the measurements due to the variation in the gap volume. For both pulse sequences, the deviation between the gap volumes is least for the ~1 second read pulse, and largest for the 15 second read pulse. These results further establish the benefit of utilizing a DBL with a short pulse length in accord with the present invention.

In addition to the hematocrit effect and variances in gap volumes, when the measurable species present in the gap 56 (FIG. 8) is measured, positive errors in the analyte reading may be introduced if the liquid sample moves during the measurement. This movement of the sample can introduce fresh analyte to the region around the working electrode where a constant diffusion pattern was already in place, thus skewing the measurement. By measuring the measurable species internal to the DBL, which has a relatively constant diffusion rate, with a short read pulse, while substantially excluding from measurement the varying diffusion rate measurable species external to the DBL, the present invention may further reduce measurement errors introduced by movement of the sample.

In order to provide a clear and consistent understanding of the specification and claims, the following definitions are provided.

The term "system" is defined as an electrochemical sensor strip in electrical communication through its conductors with an electronic measurement device, which allows for the quantification of an analyte in a sample.

The term "measurement device" is defined as an electronic device that can apply an electric potential to the conductors of an electrochemical sensor strip and measure the subsequent electrical currents. The measurement device also may include the processing capability to determine the presence and/or concentration of one or more analytes in response to the measured electric potential.

The term "sample" is defined as a composition containing an unknown amount of the analyte of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

The term "analyte" is defined as one or more substances present in the sample. The measurement process determines the presence, amount, quantity, or concentration of the analyte present in the sample. An analyte may interact with an enzyme or other species that is present during the analysis.

The term "accuracy" is defined as how close the amount of analyte measured by a sensor strip corresponds to the true amount of analyte in the sample.

The term "precision" is defined as how close multiple analyte measurements are for the same sample.

The term "conductor" is defined as an electrically conductive substance that remains stationary during an electrochemical analysis. Examples of conductor materials include solid metals, metal pastes, conductive carbon, conductive carbon pastes, and conductive polymers.

The term "non-ionizing material" is defined as a material that does not ionize during the electrochemical analysis of an analyte. Examples of non-ionizing materials include carbon, gold, platinum and palladium.

The term "measurable species" is defined as any electrochemically active species that may be oxidized or reduced under an appropriate potential at the electrode surface of an electrochemical sensor strip. Examples of measurable species include an analyte, a substrate, or a mediator.

The term "steady-state" is defined as when the rate of diffusion of the measurable species into the DBL is substantially constant.

The term "oxidoreductase" is defined as any enzyme that facilitates the oxidation or reduction of a measurable species. An oxidoreductase is a reagent. The term oxidoreductase includes "oxidases," which facilitate oxidation reactions where molecular oxygen is the electron acceptor; "reductases," which facilitate reduction reactions where the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

The term "mediator" is defined as a substance that can be oxidized or reduced and that can transfer one or more electrons between a first substance and a second substance. A mediator is a reagent in an electrochemical analysis and is not the analyte of interest, but provides for the indirect measurement of the analyte. In a simplistic system, the mediator undergoes a redox reaction with the oxidoreductase after the oxidoreductase has been reduced or oxidized through its contact with an appropriate analyte or substrate. This oxidized or reduced mediator then undergoes the opposite reaction at the working electrode and is regenerated to its original oxidation number.

The term "electro-active organic molecule" is defined as an organic molecule that does not contain a metal and that is capable of undergoing an oxidation or reduction reaction. Electro-active organic molecules can behave as redox species and as mediators. Examples of electro-active organic molecules include coenzyme pyrroloquinoline quinone (PQQ), benzoquinones and naphthoquinones, N-oxides, nitroso compounds, hydroxylamines, oxines, flavins, phenazines, phenothiazines, indophenols, and indamines.

The term "binder" is defined as a material that is chemically compatible with the reagents utilized in the reagent layer of the working electrode and that provides physical support to the reagents, while containing the reagents on the electrode conductor.

The term "average initial thickness" refers to the average height of a layer in its dry state prior to introduction of a liquid sample. The term average is used because the top surface of the layer is uneven, having peaks and valleys.

The term "redox reaction" is defined as a chemical reaction between two species involving the transfer of at least one electron from a first species to a second species. Thus, a redox reaction includes an oxidation and a reduction. The oxidation portion of the reaction involves the loss of at least one electron by the first species, and the reduction portion involves the addition of at least one electron to the second species. The ionic charge of a species that is oxidized is made more positive by an amount equal to the number of electrons transferred. Likewise, the ionic charge of a species that is reduced is made less positive by an amount equal to the number of electrons transferred.

The term "oxidation number" is defined as the formal ionic charge of a chemical species, such as an atom. A higher oxidation number, such as (III), is more positive, and a lower oxidation number, such as (II), is less positive. A neutral species has an ionic charge of zero (0). The oxidation of a species results in an increase in the oxidation number of that species, and reduction of a species results in a decrease in the oxidation number of that species.

The term "redox pair" is defined as two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidizable species" is defined as the species of a redox pair having the lower oxidation number, and which is thus capable of being oxidized into the species having the higher oxidation number. Likewise, the term "reducible species" is defined as the species of a redox pair having the higher oxidation number, and which is thus capable of being reduced into the species having the lower oxidation number.

The term "soluble redox species" is defined as a substance that is capable of undergoing oxidation or reduction and that is soluble in water (pH 7, 25° C.) at a level of at least 1.0 grams per Liter. Soluble redox species include electro-active organic molecules, organotransition metal complexes, and transition metal coordination complexes. The term "soluble redox species" excludes elemental metals and lone metal ions, especially those that are insoluble or sparingly soluble in water.

The term "organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms of the cyano groups.

The term "coordination complex" is defined as a complex having well-defined coordination geometry, such as octahedral or square planar geometry. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine is a coordination complex having a well-defined octahedral geometry where six $NH_3$ ligands (formal charge of 0 on each of the 6 ligands) are datively bonded to the ruthenium center. A more complete discussion of organotransition metal complexes, coordination complexes, and transition metal bonding may be found in Collman et al., *Principles and Applications of Organotransition Metal Chemistry* (1987) and Miessler & Tarr, Inorganic Chemistry (1991).

The term "on" is defined as "above" and is relative to the orientation being described. For example, if a first element is deposited over at least a portion of a second element, the first element is said to be "deposited on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating can be described as "on" the first element. Thus, the use of the term "on" may or may not mean that the two elements being related are in physical contact with each other.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An electrochemical system, for determining the concentration of an analyte in a sample, comprising:
   a sensor, including:
   a base;
   a first electrode on the base, the first electrode having at least one first layer on a first conductor, the first conductor on the base,
   where the first layer has an average initial thickness of less than 30 μm, and
   where the first layer includes at least one binder forming a diffusion barrier layer, the diffusion barrier layer having an internal volume, and
   where the binder includes a polymeric material that is at least partially water soluble; and
   a second electrode; and
   a measurement device,
   the measurement device in electrical communication with the first electrode through the first conductor, and the measurement device in electrical communication with the second electrode through a second conductor,
   where the measurement device applies a read pulse to the sensor, the read pulse having a duration of less than 5 seconds.

2. The electrochemical system of claim 1, where the first layer is a reagent layer including at least one of an oxidoreductase enzyme and a mediator.

3. The electrochemical system of claim 1, where the second electrode comprises the first layer on the second conductor, the second conductor on the base.

4. The electrochemical system of claim 3, where the duration of the read pulse is less than 3 seconds.

5. The electrochemical system of claim 3, where the duration of the read pulse is from 0.05 second to 2.8 seconds.

6. The electrochemical system of claim 3, where the duration of the read pulse is from 0.1 second to 1.5 seconds.

7. The electrochemical system of claim 3, where at least 50% of the average initial thickness of the first layer remains on the conductor 5 seconds after a sample is introduced to the sensor.

8. The electrochemical system of claim 1, where the duration of the read pulse is less than 3 seconds.

9. The electrochemical system of claim 8, where the average initial thickness of the first layer is at least 1 μm.

10. The electrochemical system of claim 8, where the average initial thickness of the first layer is from 5 to 25 μm.

11. The electrochemical system of claim 8, where at least 50% of the average initial thickness of the first layer remains on the conductor 5 seconds after a sample is introduced to the sensor.

12. The electrochemical system of claim 1, where the duration of the read pulse is from 0.05 second to 2.8 seconds.

13. The electrochemical system of claim 1, where the duration of the read pulse is from 0.1 second to 1.5 seconds.

14. The electrochemical system of claim 8, where the average initial thickness of the first layer is at least 1 μm.

15. The electrochemical system of claim 1, where the average initial thickness of the first layer is from 5 to 25 μm.

16. The electrochemical system of claim 1, where at least 50% of the average initial thickness of the first layer remains on the conductor 5 seconds after a sample is introduced to the sensor.

17. The electrochemical system of claim 8, where from 70% to 80% of the average initial thickness of the first layer remains on the conductor 5 seconds after a sample is introduced to the sensor.

18. The electrochemical system of claim 1, where the first electrode further comprises a reagent layer on the first layer, the reagent layer including at least one of an oxidoreductase enzyme and a mediator;
where the first layer is a distinct layer that does not include a substantial amount of at least one of an oxidoreductase and a mediator.

19. The electrochemical system of claim 1, where the polymeric material includes at least one of poly(ethylene oxide), carboxy methyl cellulose, hydroxyethyl cellulose, hydroxypropyl cellulose, polyvinyl alcohol, polyvinyl pyrrolidone, derivatives thereof, and combinations thereof.

20. The electrochemical system of claim 1, further comprising a sample in electrical communication with the first and second electrodes.

21. The electrochemical system of claim 20, where the read pulse substantially detects a measurable species within the diffusion barrier layer, and where the read pulse substantially does not detect the measurable species external to the diffusion barrier layer.

22. The electrochemical system of claim 1, where, for a plurality of sensors, at least 50% of the average initial thickness of the first layer remains on the conductor 5 seconds after a sample is introduced to the sensor.

* * * * *